US012758637B2

(12) United States Patent
Yu et al.

(10) Patent No.: US 12,758,637 B2
(45) Date of Patent: Oct. 13, 2026

(54) BIOCOMPATIBLE MATERIAL AND METHODS FOR MAKING AND USING THE SAME

(71) Applicant: PLERYON THERAPEUTICS (HANGZHOU) LIMITED, Hangzhou (CN)

(72) Inventors: Yu Yu, Shenzhen (CN); Guanqun Zhou, Shenzhen (CN); Zhexun Sun, Shenzhen (CN)

(73) Assignee: PLERYON THERAPEUTICS (HANGZHOU) LIMITED, Hangzhou (CN)

( * ) Notice: Subject to any disclaimer, the term of this patent is extended or adjusted under 35 U.S.C. 154(b) by 894 days.

(21) Appl. No.: 17/920,266

(22) PCT Filed: Apr. 22, 2021

(86) PCT No.: PCT/CN2021/088989

§ 371 (c)(1),
(2) Date: Oct. 20, 2022

(87) PCT Pub. No.: WO2021/213467

PCT Pub. Date: Oct. 28, 2021

(65) Prior Publication Data

US 2023/0173074 A1 Jun. 8, 2023

(30) Foreign Application Priority Data

Apr. 23, 2020 (WO) ................ PCT/CN2020/086487

(51) Int. Cl.

| | |
|---|---|
| ***A61K 47/36*** | (2006.01) |
| ***A61K 9/00*** | (2006.01) |
| ***C08B 37/02*** | (2006.01) |
| ***C08B 37/08*** | (2006.01) |

(52) U.S. Cl.

CPC ............ *A61K 47/36* (2013.01); *A61K 9/0019* (2013.01); *C08B 37/0021* (2013.01); *C08B 37/0072* (2013.01)

(58) Field of Classification Search

None

See application file for complete search history.

(56) References Cited

U.S. PATENT DOCUMENTS

| | | | | |
|---|---|---|---|---|
| 6,387,413 | B1 * | 5/2002 | Miyata | A61L 31/042 424/548 |
| 9,895,394 | B2 | 2/2018 | Leung et al. | |
| 10,080,767 | B2 | 9/2018 | Lebreton | |
| 2015/0087724 | A1 * | 3/2015 | Allen | C11D 1/146 568/616 |
| 2022/0062151 | A1 * | 3/2022 | Plitt | A61K 8/042 |

FOREIGN PATENT DOCUMENTS

| | | | | |
|---|---|---|---|---|
| CN | 101677957 | A | 3/2010 | |
| CN | 102573941 | A | 7/2012 | |
| CN | 105026480 | A | 11/2015 | |
| CN | 105209075 | A | 12/2015 | |
| CN | 105658633 | A | 6/2016 | |
| CN | 107206119 | A | 9/2017 | |
| JP | 2010532396 | A | 10/2010 | |
| JP | 2014514320 | A | 6/2014 | |
| WO | 2011014432 | A1 | 2/2011 | |
| WO | WO-2012145439 | A1 * | 10/2012 | A61P 7/04 |
| WO | 2019057035 | A1 | 1/2020 | |
| WO | 2020015737 | A1 | 1/2020 | |
| WO | 2020057548 | A1 | 3/2020 | |
| WO | 2020057606 | A1 | 3/2020 | |

OTHER PUBLICATIONS

PCT/CN2021/088989 International Search Report dated Jul. 23, 2021.
China 2021800294198 Search Report dated Feb. 28, 2024.
Office Action issued Apr. 22, 2025, in corresponding Japanese Patent Application No. 2022-564576 with English translation.
European 21792688.0 Extend European Search Report dated Apr. 19, 2024.

* cited by examiner

*Primary Examiner* — Dale R Miller
(74) *Attorney, Agent, or Firm* — Merchant & Gould P.C.; Daniel J. Pereira

(57) ABSTRACT

The present disclosure provides a composition comprising a first polymer with a high intrinsic viscosity [η] of at least 500 ml/g and a second polymer with a low intrinsic viscosity [η] lower than the first polymer and less than 1800 ml/g. More specifically, the present disclosure provides a hydrogel formed with the composition and a pharmaceutical, as well as a method for generating a hydrogel.

15 Claims, 16 Drawing Sheets

Specification includes a Sequence Listing.

B

A

SEQUENCE LISTING

<160> NUMBER OF SEQ ID NOS: 1

<210> SEQ ID NO 1
<211> LENGTH: 27
<212> TYPE: RNA
<213> ORGANISM: Artificial Sequence
<220> FEATURE:
<223> OTHER INFORMATION: aptamer
<220> FEATURE:
<221> NAME/KEY: modified_base
<222> LOCATION: (1)..(1)
<223> OTHER INFORMATION: c represents 2-fluoro variant of cytidylic acid
<220> FEATURE:
<221> NAME/KEY: modified_base
<222> LOCATION: (2)..(2)
<223> OTHER INFORMATION: g represents 2-methoxy variant of guanylic acid
<220> FEATURE:
<221> NAME/KEY: modified_base
<222> LOCATION: (3)..(3)
<223> OTHER INFORMATION: g represents 2-methoxy variant of guanylic acid
<220> FEATURE:
<221> NAME/KEY: modified_base
<222> LOCATION: (6)..(6)
<223> OTHER INFORMATION: u represents 2-fluoro variant of uridylic acid
<220> FEATURE:
<221> NAME/KEY: modified_base
<222> LOCATION: (7)..(7)
<223> OTHER INFORMATION: c represents 2-fluoro variant of cytidylic acid
<220> FEATURE:
<221> NAME/KEY: modified_base
<222> LOCATION: (8)..(8)
<223> OTHER INFORMATION: a represents 2-methoxy variant of adenylic acid
<220> FEATURE:
<221> NAME/KEY: modified_base
<222> LOCATION: (9)..(9)
<223> OTHER INFORMATION: g represents 2-methoxy variant of guanylic acid
<220> FEATURE:
<221> NAME/KEY: modified_base
<222> LOCATION: (10)..(10)
<223> OTHER INFORMATION: u represents 2-fluoro variant of uridylic acid
<220> FEATURE:
<221> NAME/KEY: modified_base
<222> LOCATION: (11)..(11)
<223> OTHER INFORMATION: g represents 2-methoxy variant of guanylic acid
<220> FEATURE:
<221> NAME/KEY: modified_base
<222> LOCATION: (12)..(12)
<223> OTHER INFORMATION: a represents 2-methoxy variant of adenylic acid
<220> FEATURE:
<221> NAME/KEY: modified_base
<222> LOCATION: (13)..(13)
<223> OTHER INFORMATION: a represents 2-methoxy variant of adenylic acid
<220> FEATURE:
<221> NAME/KEY: modified_base
<222> LOCATION: (14)..(14)
<223> OTHER INFORMATION: u represents 2-fluoro variant of uridylic acid
<220> FEATURE:
<221> NAME/KEY: modified_base
<222> LOCATION: (15)..(15)
<223> OTHER INFORMATION: g represents 2-methoxy variant of guanylic acid
<220> FEATURE:
<221> NAME/KEY: modified_base
<222> LOCATION: (16)..(16)
<223> OTHER INFORMATION: c represents 2-fluoro variant of cytidylic acid
<220> FEATURE:

-continued

```
<221> NAME/KEY: modified_base
<222> LOCATION: (17)..(17)
<223> OTHER INFORMATION: u represents 2-fluoro variant of uridylic acid
<220> FEATURE:
<221> NAME/KEY: modified_base
<222> LOCATION: (18)..(18)
<223> OTHER INFORMATION: u represents 2-fluoro variant of uridylic acid
<220> FEATURE:
<221> NAME/KEY: modified_base
<222> LOCATION: (19)..(19)
<223> OTHER INFORMATION: a represents 2-methoxy variant of adenylic acid
<220> FEATURE:
<221> NAME/KEY: modified_base
<222> LOCATION: (20)..(20)
<223> OTHER INFORMATION: u represents 2-fluoro variant of uridylic acid
<220> FEATURE:
<221> NAME/KEY: modified_base
<222> LOCATION: (21)..(21)
<223> OTHER INFORMATION: a represents 2-methoxy variant of adenylic acid
<220> FEATURE:
<221> NAME/KEY: modified_base
<222> LOCATION: (22)..(22)
<223> OTHER INFORMATION: c represents 2-fluoro variant of cytidylic acid
<220> FEATURE:
<221> NAME/KEY: modified_base
<222> LOCATION: (23)..(23)
<223> OTHER INFORMATION: a represents 2-methoxy variant of adenylic acid
<220> FEATURE:
<221> NAME/KEY: modified_base
<222> LOCATION: (24)..(24)
<223> OTHER INFORMATION: u represents 2-fluoro variant of uridylic acid
<220> FEATURE:
<221> NAME/KEY: modified_base
<222> LOCATION: (25)..(25)
<223> OTHER INFORMATION: c represents 2-fluoro variant of cytidylic acid
<220> FEATURE:
<221> NAME/KEY: modified_base
<222> LOCATION: (26)..(26)
<223> OTHER INFORMATION: c represents 2-fluoro variant of cytidylic acid
<220> FEATURE:
<221> NAME/KEY: modified_base
<222> LOCATION: (27)..(27)
<223> OTHER INFORMATION: g represents 2-methoxy variant of guanylic acid

<400> SEQUENCE: 1

cggaaucagu gaaugcuuau acauccg                              27
```

BIOCOMPATIBLE MATERIAL AND METHODS FOR MAKING AND USING THE SAME

CROSS REFERENCE TO RELATED APPLICATIONS

This application is a National Stage Application and claims priority under 35 U.S.C. § 371 to Patent Cooperation Treaty application PCT/CN2021/088989, filed Apr. 22, 2021, which claims the benefit of Patent Cooperation Treaty application PCT/CN2020/086487, filed Apr. 23, 2020. Priority is claimed to these applications and the disclosure of these prior applications is considered part of the disclosure of this application and to the extent allowed the entire contents of the aforementioned applications are incorporated herein.

SEQUENCE LISTING

This application incorporates by reference in its entirety the Sequence Listing entitled "2022 Oct. 20_262790-517080_ST25", is 3,146 bytes in size and was created on Oct. 20, 2022, and filed electronically herewith.

A chemically crosslinked polymer-polymer hydrogel is formed by crosslinking one polymer with another polymer. The polymers are usually modified with a reactive group, and crosslinks by a chemical reaction.

There are two major types of crosslinking. One is to crosslink the polymer with small molecule crosslinker. But small molecules may be toxic to the human body and may cause undesirable reactions, thus are not suitable in many occasions. Another type of crosslinking is to grafted reactive groups on different polymers, and the polymers grafted with different reactive groups may react and form hydrogel. This type of crosslinking is able to generate hydrogel of desirable properties, for example hydrogel of low mechanical strength. Previous work suggest that a hydrogel of low mechanical strength can be made by reacting one or more reactive polymers of large radius of gyration (Rg), large intrinsic viscosity ([η]) or high molecular weight (MW).

Thus, there is a need to generate hydrogels having desired properties with properly stable polymers required for product manufacturing.

SUMMARY OF THE INVENTION

The present disclosure provides compositions comprising a polymer (e.g., a biocompatible polymer) capable of forming a hydrogel and methods for making and using the same. For example, the composition may comprise at least a first polymer and at least a second polymer, wherein the first polymer may have an intrinsic viscosity [η] of at least 500 ml/g in the composition, and the second polymer may have an intrinsic viscosity [η] of lower than the first polymer and less than 1800 ml/g (e.g., as measured by a Ubbelohde viscometer). A concentration of the first polymer in the composition may be at most about 5 mg/ml. The first polymer and the second polymer are stable in the composition for a long-term storage (e.g., for 24 hours or longer) for appropriate quality control testing and transportation. The composition as well as the polymers in it are useful to be formed a hydrogel product that can be manufactured. The hydrogel formed by the first polymer and/or the second polymer may encapsulate a bioactive agent (e.g., a drug). And the bioactive agent can be cumulatively released from the hydrogel.

Further, the present disclosure provides a hydrogel formed by the polymer of the present disclosure. In some cases, the hydrogel may be viscoelastic solid at a relatively low G' value and have a higher G' comparing to G". In some cases, the hydrogel may be relatively more elastic at a lower stress level, but relatively more viscous at a higher stress level. In some specifical cases, the hydrogel having a high elasticity at low stress may not necessarily correspond to a high elasticity at high stress. In some cases, the hydrogel may have a higher viscosity at low shear rate but lower viscosity at high shear rate. Accordingly, the mechanical properties (such as elastic behavior) of the hydrogel of the present disclosure under different conditions (such as strain, shear rate, frequency) can be adjustable.

In some embodiments, the first polymer of the present disclosure does not crosslink itself and the second polymer does not crosslink itself. The hydrogels formed according to the present disclosure may have a relatively low G' (e.g. with a G' less than about 5 Pa), a higher G' comparing to G" (e.g. G"/G' <1) while having relatively large yield strain (e.g., >10%). The hydrogel of the present disclosure may have a low viscosity (e.g., with a viscosity of no more than about 0.5 Pa·s) at high shear rate, indicating that it might be easy to spread across a surface with the help of only a small force.

In one aspect, the present disclosure provides a composition which comprises at least a first polymer having a first reactive group and at least a second polymer having a second reactive group, wherein said first polymer have an intrinsic viscosity [η] of at least 500 ml/g and said second polymer have an intrinsic viscosity [η] lower than the first polymer and less than 1800 ml/g, and a concentration of said first polymer in said composition is at most about 5 mg/ml.

In some embodiments, said first polymer is capable of reacting with said second polymer to form a hydrogel.

In some embodiments, said first polymer and/or said second polymer is hydrophilic and/or water soluble.

In some embodiments, said first polymer and/or said second polymer is independently selected from the group consisting of a polysaccharide, a poly (acrylic acid), a poly(hydroxyethylmethacrylate), an elastin, a collagen, a polyethylene glycol, a derivative thereof, and any combinations thereof.

In some embodiments, said first polymer and/or said second polymer is independently selected from the group consisting of a hyaluronic acid, a guar gum, a starch, a chitosan, a chondroitin sulfate, an alginate, a carboxymethylcellulose, a dextran, a derivative thereof, and any combinations thereof.

In some embodiments, said first polymer and/or said second polymer is independently selected from the group consisting of a hyaluronic acid, a dextran, a derivative thereof, and any combinations thereof.

In some embodiments, said first polymer comprises a first polymer derivative, said first polymer derivative comprises a first reactive group, and said first polymer derivative is electrophilic.

In some embodiments, said first reactive group is selected from the group consisting of a vinyl, an acryloyl, a thiol, an alkene, a thiolester, an isocyanate, an isothiocyanate, an alkyl halide, a sulfonyl halide, an epoxide, an imidoester, a fluorophenyl ester, a carbonate, a carbodiimide, a disulfide, an aziridine and any combinations thereof.

In some embodiments, said first reactive group is selected from a vinylsulfone, a maleimide, an acrylate, a methacrylate, an epoxide and any combinations thereof.

In some embodiments, said second polymer comprises a second polymer derivative, said second polymer derivative comprises a second reactive group, and said second polymer derivative is nucleophilic.

In some embodiments, said second reactive group is selected from the group consisting of a thiol, an amine, an azide, a hydrazide, a diene, a hydrazine, a hydroxylamine and any combinations thereof.

In some embodiments, said first polymer has a molecular weight of about 500,000 to about 5,500,000 dalton.

In some embodiments, said second polymer has a molecular weight of about 3,000 to about 800,000 dalton.

In some embodiments, a molecular weight (MW) ratio between said first polymer and said second polymer in said composition is from about 500:1 to about 1.5:1.

In some embodiments, a radius of gyration (Rg) ratio between said first polymer and said second polymer in said composition is from about 150:1 to about 1:1.

In some embodiments, a mass ratio between said first polymer and said second polymer in said composition is from about 20:1 to about 1:20.

In some embodiments, a molar ratio between said first polymer and said second polymer in said composition is from about 4:1 to about 1:500.

In some embodiments, said first polymer may have an intrinsic viscosity [η] of from about 500 ml/g to about 5000 ml/g In some embodiments, said second polymer may have an intrinsic viscosity [η] of from about 5 ml/g to about 1800 ml/g In some embodiments, the ratio between the intrinsic viscosity of first polymer and said second polymer in said composition is from about 500:1 to about 1:1.

In some embodiments, said derivative has an average degree of modification (DM) of about 3% to about 50%.

In some embodiments, said first polymer derivative has a first DM, said second polymer derivative has a second DM, and a ratio between said first DM and said second DM is from about 20:1 to about 1:20.

In some embodiments, said first polymer derivative is a hyaluronic acid derivative modified with one or more vinylsulfone groups, a hyaluronic acid derivative modified with one or more maleimide groups, or a combination thereof, and said second polymer derivative is a dextran derivative modified with one or more thiol groups, a hyaluronic acid derivative modified with one or more thiol groups, a polyethylene glycol derivative modified with one or more thiol groups or a combination thereof.

In some embodiments, said first polymer and or said second polymer is comprised in said composition in a hydrogel formed.

In some embodiments, said composition does not comprise any crosslinker different from said first polymer and/or second polymer.

In another aspect, the present disclosure provides a hydrogel formed with the composition of the present disclosure.

In some embodiments, said hydrogel of the present disclosure is biocompatible.

In some embodiments, said hydrogel has at least one of the followings properties: 1) a storage modulus G' that is no more than 5 Pa, as measured in a dynamic oscillatory shear test at 5% strain and 5 rad/s frequency; 2) a viscosity that is no more than about 0.5 Pa·s as measured in a continuous shear test at a shear rate of more than about 100/s; and 3) a loss modulus G" that is no more than about 100% of its storage modulus G', as measured in a dynamic oscillatory shear test at 5% strain and 5 rad/s frequency.

In another aspect, the present disclosure provides a method for generating a hydrogel, comprising: a) providing the composition of the present disclosure; and b) subjecting said composition to a condition enabling formation of the hydrogel.

In some embodiments, said subjecting comprises incubating said composition at about 15° C. to about 50° C.

In another aspect, the present disclosure provides a pharmaceutical composition comprising the hydrogel of the present disclosure.

In some embodiments, said hydrogel is formulated to be suitable as a drug encapsulation.

In some embodiments, said pharmaceutical composition comprises a drug, and said drug is encapsulated in said hydrogel.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are employed, and the accompanying drawings (also "figure" and "FIG." herein), of which:

DETAILED DESCRIPTION

Figure 1:
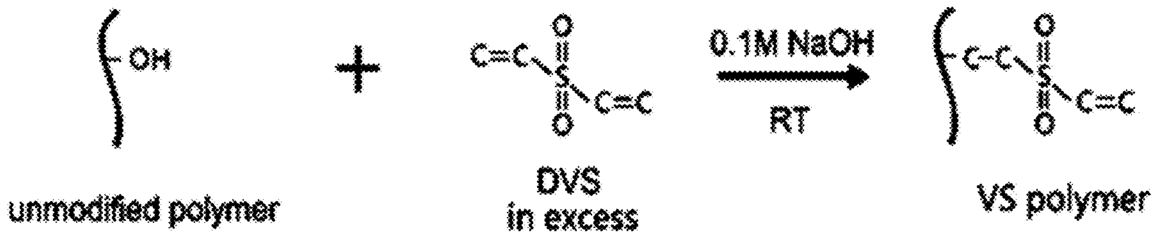
FIG. 1 illustrates the synthesis of HA-VS polymer.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "polymer", as used herein, generally refers to a chemical compound or mixture of compounds formed by polymerization and consisting essentially of repeating structural units. In some embodiments, the polymer may be a hydrogel forming polymer. The term "hydrogel forming polymer", as used herein, generally refers to a polymer participating in the formation of a hydrogel. It may be a naturally occurring polymer or a synthetic polymer capable of forming a hydrogel. The hydrogel forming polymer may include polymer(s) making a contribution to hydrogel formation. In some embodiments, the hydrogel forming polymer does not include polymers that are not able to participate in hydrogel formation, and/or polymers unable to form a hydrogel, even if present in the composition of the present disclosure. In some cases, the hydrogel forming polymer may also be referred to as "a backbone polymer" and "crosslinker polymer".

The term "hydrogel", as used herein, generally refers to a gel or gel-like structure comprising one or more polymers suspended in an aqueous solution (e.g., water). All hydrogels possess some level of physical attraction between macromers as a result of entanglements amongst one another. Usually a hydrogel intended for tissue engineering applications may be strengthened through additional physical interactions or chemical cross-linking.

The term "electrophilic", as used herein, generally refers to having an affinity for electron pairs. An electrophilic substance (e.g., molecule or portion of a molecule) may be an electron pair acceptor. In some embodiments, an electrophilic molecule or group may be selected from the group consisting of a vinyl, an acryloyl, a thiol, an alkene, a thiolester, an isocyanate, an isothiocyanate, an alkyl halide, a sulfonyl halide, an epoxide, an imidoester, a fluorophenyl ester, a carbonate, a carbodiimide, a disulfide, an aziridine and any combinations thereof. In some embodiments, an electrophilic molecule or group may comprise a vinylsulfone, a maleimide, an acrylate, a methacrylate, an epoxide and any combinations thereof.

The term "nucleophilic", as used herein, generally refers to having a property of capable of donating an electron pair to form a chemical bond in relation to a reaction with electrophilic substances. In some embodiments, the term may refer to a substance's nucleophilic character and an affinity for electriphiles. In some embodiments, a nucleophilic substance (e.g., molecule or portion of a molecule) may be selected from the group consisting of a thiol, an amine, an azide, a hydrazide, an amine, a diene, a hydrazine, a hydroxylamine and any combinations thereof.

The term "hydrophilic", as used herein, generally refers to having an affinity for water, able to absorb or be wetted by water. A hydrophilic molecule or portion of a molecule is one whose interactions with water and other polar substances are more thermodynamically favorable than their interactions with oil or other hydrophobic solvents.

The term "viscosity", as used herein, generally refers to a property of resistance to flow in a fluid or semifluid.

The term "intrinsic viscosity [η]", as used herein, generally refers a value measured from a dilute solution of macromolecules contains information on the macromolecular shape, flexibility, and molar mass of macromolecules. It is defined as the reduced specific viscosity in the limit of "infinite dilution" or zero concentration. In the present disclosure, the intrinsic viscosity [η] may be measured by a Ubbelohde viscometer, or a differential viscometer. Alternatively, the intrinsic viscosity [η] may be calculated from Mark-Houwink equation from established relation between intrinsic viscosity and molecular weight. The [η] of a polymer may be different in different conditions, for examples at different solvent, a solvent of a different composition (e.g. different salt concentration), or different temperature. If not specified, the [η] value in this patent is referring to the [η] at the hydrogel forming condition.

The term "substantial", as used herein, generally refers to more than a minimal or insignificant amount; and "substantially" generally refers to more than minimally or insignificantly.

The term "storage modulus G'", as used herein, generally represents the elastic response of a material to an oscillatory sinusoidal strain as measured by a dynamic oscillatory mode of a rheometer.

The term "loss modulus G"", as used herein, generally represent the viscous response of a material to a oscillatory sinusoidal strain as measured by a dynamic oscillatory mode of a rheometer.

The term "average degree of modification (DM)", as used herein, generally refers to the number of reactive groups per 100 repeating unit in a polymer. In the present disclosure, the reactive may be added to a polymer before or after the polymer is generated. In some embodiments, the reactive group may be added to a polymer during a preparation process of the polymer. In some embodiments, the reactive group may be added to the polymer during a modification process. For example, a DM may reflect the degrees of modification of a polymer derivative.

The term "radius of gyration (Rg)" or "gyradius" of a polymer, as used herein, generally refers to the average distance of a polymer chain element from the center of gravity of the chain.

The term "crosslink", as used herein, generally refers to a bond that links one polymer chain to another. They can be covalent bonds or ionic bonds. "Polymer chains" may refer to synthetic polymers or natural polymers (such as hyaluronic acid).

The term "crosslinker", as used herein, generally refers to an agent that links one polymer chain to another with bonds. The crosslinker can achieve crosslink through covalent bonds or noncovalent bonds. The "polymer chains" may refer to synthetic polymers, natural polymers (such as hyaluronic acid) or derivatives of natural polymers. In polymer chemistry, when a polymer is the to be "cross-linked", it usually means that the entire bulk of the polymer has been exposed to the cross-linking method. The resulting modification of mechanical properties depends strongly on the cross-link density. Crosslinks may be formed by chemical reactions between polymers.

The term "precursor polymer", as used herein, generally refers to a polymer used to form another polymer structure or to be further modified. This material is capable of further polymerization by reactive groups to form structures of higher molecular weight.

The term "composition", as used herein, generally refers to a product (liquid or solid-state) of various elements or ingredients.

The term "biocompatible" or "biocompatibility", as used herein, generally refers to a condition of being compatible with a living tissue or a living system by not being toxic, injurious, or physiologically reactive and/or not causing immunological rejection.

The term "about", when used in the context of numerical values, generally refers to a value less than 1% to 15% (e.g., less than 1%, less than 2%, less than 3%, less than 4%, less than 5%, less than 6%, less than 7%, less than 8%, less than 9%, less than 10%, less than 11%, less than 12%, less than 13%, less than 14%, or less than 15%) above or below an indicated value.

Where a range of values (e.g., a numerical range) is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

As used herein, the singular forms "a," "and," and "the" include plural referents unless the context clearly dictates otherwise. Thus, for example, reference to "a particle" includes a plurality of such particles and reference to "the sequence" includes reference to one or more said sequences and equivalents thereof known to those skilled in the art, and so forth.

As will be understood by those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible. This is intended to provide support for all such combinations.

The present disclosure provides compositions comprising one or more hydrogel forming polymers and methods for making and using the same. And the present disclosure provides a hydrogel and methods for making and using the same.

In one aspect, the present disclosure provides a composition which may comprise at least a (e.g., one, two, three, four, five, six, seven, eight, night, ten or more) first polymer with a high intrinsic viscosity [η] and at least a (e.g., one, two, three, four, five, six, seven, eight, night, ten or more) second polymer with a low intrinsic viscosity [η]. In some embodiments, said first polymer may have a [η] of at least about 500 ml/g (e.g., at least about 500 ml/g, at least about 600 ml/g, at least about 700 ml/g, at least about 800 ml/g, at least about 900 ml/g, at least about 1000 ml/g, at least about 1100 ml/g, at least about 1200 ml/g, at least about 1300 ml/g, at least about 1400 ml/g, at least about 1500 ml/g, at least about 1600 ml/g, at least about 1700 ml/g, at least about 1800 ml/g, at least about 1900 ml/g, at least about 2000 ml/g, at least about 2200 ml/g, at least about 2400 ml/g, at least about 2800 ml/g, at least about 2900 ml/g, at least about 3000 ml/g, at least about 3500 ml/g, at least about 4000 ml/g, at least about 4500 ml/g, at least about 5000 ml/g or higher), and said second polymer may have a [η] of lower than the first polymer and less than about 1800 ml/g (e.g., less than about 1700 ml/g, less than about 1600 ml/g, less than about 1500 ml/g, less than about 1400 ml/g, less than about 1300 ml/g, less than about 1200 ml/g, less than about 1100 ml/g, less than about 1000 ml/g, less than about 900 ml/g, less than about 800 ml/g, less than about 700 ml/g, less than about 600 ml/g, less than about 500 ml/g, less than about 400 ml/g, less than about 300 ml/g, less than about 200 ml/g, less than about 100 ml/g, less than about 20 ml/g, less than about 10 ml/g, or lower).

In some embodiments, said first polymer may have an intrinsic viscosity [η] of from about 500 ml/g to about 5000 ml/g (e.g., from about 500 ml/g to about 4600 ml/g, from about 600 ml/g to about 4400 ml/g, from about 800 ml/g to about 4200 ml/g, from about 1000 ml/g to about 4000 ml/g, from about 1500 ml/g to about 3500 ml/g, from about 2000 ml/g to about 3500 ml/g from about 2500 ml/g to about 3500 ml/g, etc). In some embodiments, said first polymer may have an intrinsic viscosity [η] of from about 1000 ml/g to about 4000 ml/g, for example, said first polymer may have an intrinsic viscosity [η] of from about 2500 ml/g to about 3500 ml/g as measured by a Ubbelohde viscometer, a hydrogel permeation chromatography coupled with a capillary viscometer, or calculated based on published relation between molecular weight and [η].

In some embodiments, said second polymer may have an intrinsic viscosity [η] of from about 5 ml/g to about 1800 ml/g (e.g., from about 5 ml/g to about 1600 ml/g, from about 5 ml/g to about 1400 ml/g, from about 5 ml/g to about 1200 ml/g, from about 5 ml/g to about 1000 ml/g, from about 5 ml/g to about 500 ml/g, from about 5 ml/g to about 400 ml/g, from about 5 ml/g to about 300 ml/g, from about 5 ml/g to about 250 ml/g, from about 10 ml/g to about 200 ml/g, from about 10 ml/g to about 150 ml/g, from about 15 ml/g to about 100 ml/g, etc). In some embodiments, the [η] may be measured by a Ubbelohde viscometer. For example, said second polymer may have an intrinsic viscosity [η] of from about 5 ml/g to about 200 ml/g as measured by a Ubbelohde viscometer, a hydrogel permeation chromatography coupled with a capillary viscometer, or calculated based on published relation between molecular weight and [η].

In some embodiments, said first polymer may have an intrinsic viscosity [n] of from about 1000 ml/g to about 4000 ml/g and said second polymer may have an intrinsic viscosity [n] of from about 5 ml/g to about 200 ml/g.

In the present disclosure, the first polymer has a first intrinsic viscosity [η] (H1), and the second polymer has a second intrinsic viscosity [η] (H2). In some embodiments, the [η]1 may be larger than the [η]2 and a ratio between the H1 and the [η]2 may be from about 500:1 to about 1:1 (e.g., from about 500:1 to about 1:1, from about 400:1 to about 1:1, from about 300:1 to about 1:1, from about 200:1 to about 1:1, from about 100:1 to about 1:1, from about 50:1 to about 1:1, from about 3:1 to about 1:1, from about 20:1 to about 1:1, from about 10:1 to about 1:1, from about 5:1 to about 1:1, from about 500:1 to about 10:1, from about 500:1 to about 40:1, from about 500:1 to about 50:1, from about 500:1 to about 100:1, from about 500:1 to about 200:1, from about 500:1 to about 300:1, from about 500:1 to about 400:1, from about 400:1 to about 20:1, from about 250:1 to about 30:1, from about 150:1 to about 40:1, etc.), For example, a ratio between the [η]1 and the [η]2 may be from about 300:1 to about 25:1.

In some embodiments, said first polymer's concentration in said composition may be at most about 5 mg/ml. In some embodiments, said first polymer's concentration in said composition may be from about 0.1 mg/ml to about 4 mg/ml (e.g., from about 0.1 mg/ml to about 4 mg/ml, from about 0.2 mg/ml to about 3 mg/ml, from about 0.3 mg/ml to about 2 mg/ml, from about 0.3 mg/ml to about 1.5 mg/ml, etc.). In some embodiments, said first polymer's concentration in said composition may be from about 0.3 mg/ml to about 1.5 mg/ml In some embodiments, said first polymer may be selected from the group consisting of a polysaccharide, a poly (acrylic acid), a poly(hydroxyethylmethacrylate), an elastin, a collagen, a polyethylene glycol, a derivative thereof, and any combinations thereof. For example, the first polymer in the composition may comprise one or more of the following: a polysaccharide, one or more types of polysaccharide derivative, a poly (acrylic acid), one or more types of poly (acrylic acid) derivative, a poly (hydroxyethylmethacrylate), one or more types of poly (hydroxyethylmethacrylate) derivative, an elastin, one or more types of elastin derivative, a collagen, one or more types of collagen derivative, a polyethylene glycol and one or more types of a polyethylene glycol derivative and any combinations thereof.

In some embodiments, said second polymer may be selected from the group consisting of a polysaccharide, a poly (acrylic acid), a poly(hydroxyethylmethacrylate), an elastin, a collagen, a polyethylene glycol, a derivative thereof, and any combinations thereof. For example, the second polymer in the composition may comprise one or more of the following: a polysaccharide, one or more types of polysaccharide derivative, a poly (acrylic acid), one or more types of poly (acrylic acid) derivative, a poly (hydroxyethylmethacrylate), one or more types of poly (hydroxyethylmethacrylate) derivative, an elastin, one or more types of elastin derivative, a collagen, one or more types of collagen derivative, a polyethylene glycol and one or more types of a polyethylene glycol derivative and any combinations thereof.

In some embodiments, said first polymer may be selected from the group consisting of a polysaccharide, a poly (acrylic acid), a poly(hydroxyethylmethacrylate), an elastin, a collagen, a polyethylene glycol, a derivative thereof, and any combinations thereof, and said second polymer may be selected from the group consisting of a polysaccharide, a poly (acrylic acid), a poly(hydroxyethylmethacrylate), an elastin, a collagen, a polyethylene glycol, a derivative thereof, and any combinations thereof.

In some embodiments, said first polymer may be selected from the group consisting of a hyaluronic acid, a guar gum, a starch, a chitosan, a chondroitin sulfate, an alginate, a carboxymethylcellulose, a dextran, a derivative thereof, and any combinations thereof. For example, the first polymer in the composition may comprise one or more of the following: a hyaluronic acid, one or more types of hyaluronic acid derivative, a guar gum, one or more types of guar gum derivative, a starch, one or more types of starch derivative, a chitosan, one or more types of chitosan derivative, a chondroitin sulfate, one or more types of chondroitin sulfate derivative, an alginate, one or more types of alginate derivative, a carboxymethylcellulose and one or more types of carboxymethylcellulose derivative, a dextran, one or more types of dextran derivative, and any combinations thereof.

In some embodiments, said second polymer may be selected from the group consisting of a hyaluronic acid, a guar gum, a starch, a chitosan, a chondroitin sulfate, an alginate, a carboxymethylcellulose, a dextran, a derivative thereof, and any combinations thereof. For example, the second polymer in the composition may comprise one or more of the following: a hyaluronic acid, one or more types of hyaluronic acid derivative, a guar gum, one or more types of guar gum derivative, a starch, one or more types of starch derivative, a chitosan, one or more types of chitosan derivative, a chondroitin sulfate, one or more types of chondroitin sulfate derivative, an alginate, one or more types of alginate derivative, a carboxymethylcellulose and one or more types of carboxymethylcellulose derivative, a dextran, one or more types of dextran derivative, a polyethylene glycol, one or more types of polyethylene glycol derivative, and any combinations thereof.

In some embodiments, said first polymer may be selected from the group consisting of a hyaluronic acid, a guar gum, a starch, a chitosan, a chondroitin sulfate, an alginate, a carboxymethylcellulose, a dextran, a derivative thereof, and any combinations thereof, and said second polymer may be selected from the group consisting of a hyaluronic acid, a guar gum, a starch, a chitosan, a chondroitin sulfate, an alginate, a carboxymethylcellulose, a dextran, a polyethylene glycol, a derivative thereof, and any combinations thereof.

In some embodiments, said first polymer may be selected from the group consisting of a hyaluronic acid, a dextran, a derivative thereof, and any combinations thereof. For example, the first polymer in the composition may comprise one or more of the following: a hyaluronic acid, one or more types of hyaluronic acid derivative, a dextran, one or more types of dextran derivative, and any combinations thereof.

In some embodiments, said second polymer may be selected from the group consisting of a hyaluronic acid, a dextran, a derivative thereof, and any combinations thereof. For example, the second polymer in the composition may comprise one or more of the following: a hyaluronic acid, one or more types of hyaluronic acid derivative, a dextran, one or more types of dextran derivative, a polyethylene glycol, and any combinations thereof.

In some embodiments, said first polymer may be selected from the group consisting of a hyaluronic acid, a dextran, a derivative thereof, and any combinations thereof, and said second polymer may be selected from the group consisting of a hyaluronic acid, a dextran, a derivative thereof, and any combinations thereof.

For example, said first polymer in the composition may comprise one or more of the following: a hyaluronic acid derivative and the said second polymer may be a hyaluronic acid derivative. For another example, said first polymer may be a hyaluronic acid derivative and the said second polymer may be a dextran derivative.

In some embodiments, the composition of the present disclosure may comprise at least a first polymer derivative and a second polymer derivative, wherein said first polymer derivative may comprise a first reactive group and said second polymer derivative may comprise a second reactive group. The first reactive group may be different from the second reactive group.

According to any aspect of the present disclosure, the polymer (e.g., the hydrogel forming polymers) may be modified with one or more reactive groups, e.g., to become a polymer derivative of the present disclosure. In one example, a polymer of the present disclosure (e.g., the hydrogel forming polymers) may be modified with one or more vinylsulfone groups (or with a molecule comprising one or more vinylsulfone groups). In another example, a polymer of the present disclosure (e.g., the hydrogel forming polymers) may be modified with one or more thiol groups (or with a molecule comprising one or more thiol groups).

In the present disclosure, the first polymer may comprise a first polymer derivative, said first polymer derivative may comprise a first reactive group, and the first polymer derivative may be electrophilic. In some embodiments, the first reactive group may be selected from the group consisting of a vinyl, a maleimide, an acrylate, a methacrylate, an epoxide, a thiol, an alkene, a thiolester, an isocyanate, an isothiocyanate, an alkyl halide, a sulfonyl halide, an epoxide, an imidoester, a fluorophenyl ester, a carbonate, a carbodiimide, a disulfide, an aziridine and any combinations thereof. In some embodiments, the first reactive group may be selected from the group consisting of a vinyl, an acryloyl, a thiol, an alkene, a thiolester, an isocyanate, an isothiocyanate, an alkyl halide, a sulfonyl halide, an epoxide, an imidoester, a fluorophenyl ester, a carbonate, a carbodiimide, a disulfide an aziridine and any combinations thereof.

In some embodiments, said first reactive group may be selected from a vinylsulfone, a maleimide, an acrylate, a methacrylate, an epoxide and any combinations thereof.

In the present disclosure, the second polymer may comprise a second hydrogel forming polymer derivative, said second polymer derivative may comprise a second reactive group, and the second hydrogel forming polymer derivative may be nucleophilic.

In some embodiments, the second reactive group may be selected from the group consisting of a thiol, an amine, an azide, a hydrazide, a diene, a hydrazine, a hydroxylamine and any combinations thereof.

In some embodiments, the first reactive group may be selected from the group consisting of a vinyl, a maleimide, an acrylate, a methacrylate, an epoxide, a thiol, an alkene, a thiolester, an isocyanate, an isothiocyanate, an alkyl halide, a sulfonyl halide, an epoxide, an imidoester, a fluorophenyl ester, a carbonate, a carbodiimide, a disulfide, an aziridine and any combinations thereof, and the second reactive group may be selected from the group consisting of a thiol, an amine, an azide, a hydrazide, a diene, a hydrazine, a hydroxylamine and any combinations thereof.

In some embodiments, said first reactive group may be selected from a vinylsulfone, a maleimide, an acrylate, a methacrylate, an epoxide and any combinations thereof, and the second reactive group may be selected from the group consisting of a thiol, an amine, an azide, a hydrazide, a diene, a hydrazine, a hydroxylamine and any combinations thereof.

For example, the first reactive group may comprise a vinylsulfone and the second reactive group may comprise a thiol.

In some embodiment, in the composition, the first reactive group may comprise one or more vinylsulfone and the second reactive group may comprise one or more thiols.

In some embodiments, the first polymer derivative may be capable of reacting with the second polymer derivative to form the hydrogel.

In some embodiments, said first polymer may have a molecular weight of about 500,000 to about 5,500,000 dalton (e.g., about 500,000 to about 5,500,000 dalton, about 1,000,000 to about 5,500,000 dalton, about 1,500,000 to about 5,500,000 dalton, about 2,000,000 to about 5,500,000 dalton, about 2,5000,000 to about 5,500,000 dalton, about 3,000,000 to about 5,500,000 dalton, about 3,500,000 to about 5,500,000 dalton, about 4,000,000 to about 5,500,000 dalton, about 4,500,000 to about 5,500,000 dalton, or about 500,000 to about 5,000,000 dalton, about 500,000 to about 4,500,000 dalton, about 500,000 to about 4,000,000 dalton, about 500,000 to about 3,500,000 dalton, about 1,000,000 to about 3,000,000 dalton, about 1,000,000 to about 2,500,000 dalton, about 1,000,000 to about 2,000,000 dalton, about 1,000,000 to about 1,500,000 dalton, or about 1,500,000 to about 5,000,000 dalton, about 2,000,000 to about 4,500,000 dalton, about 2,000,000 to about 4,000,000 dalton, about 2,000,000 to about 3,500,000 dalton, about 2,000,000 to about 3,000,000 dalton, etc). In some embodiments, said first polymer may be a hyaluronic acid.

In some embodiments, said second polymer may have a molecular weight of about 3,000 to about 800,000 dalton (e.g., about 3,000 to about 800,000 dalton, about 5,000 to about 700,000 dalton, about 10,000 to about 600,000 dalton, about 15,000 to about 500,000 dalton, about 20,000 to about 400,000 dalton, about 20,000 to about 300,000 dalton, about 20,000 to about 200,000 dalton, about 20,000 to about 100,000 dalton, about 20,000 to about 90,000 dalton, about 20,000 to about 80,000 dalton, about 20,000 to about 70,000 dalton, about 20,000 to about 60,000 dalton, about 20,000 to about 50,000 dalton, etc). In some embodiments, said second polymer may have a molecular weight of about 20,000 to about 800,000 dalton (e.g., about 20,000 to about 800,000 dalton, about 20,000 to about 700,000 dalton, about 20,000 to about 600,000 dalton, about 20,000 to about 500,000 dalton, about 20,000 to about 400,000 dalton, about 20,000 to about 300,000 dalton, about 20,000 to about 200,000 dalton, about 20,000 to about 100,000 dalton, about 20,000 to about 90,000 dalton, about 20,000 to about 80,000 dalton, about 20,000 to about 70,000 dalton, about 20,000 to about 60,000 dalton, about 20,000 to about 50,000 dalton, etc).

In some embodiments, a molecular weight (MW) ratio between said first polymer and said second polymer in said composition may be from about 500:1 to about 1.5:1 (e.g., from about 500:1 to about 1.5:1, from about 450:1 to about 1.5:1, from about 400:1 to about 1.5:1, from about 350:1 to about 1.5:1, from about 300:1 to about 1.5:1, from about 250:1 to about 1.5:1, from about 200:1 to about 1.5:1, from about 150:1 to about 1.5:1, from about 100:1 to about 1.5:1, etc).

In the present disclosure, the first polymer in the composition may have a radius of gyration (Rg) more than about 30 nm (e.g., from about 30 nm to about 500 nm, from about 50 nm to about 450 nm, from about 100 nm to about 400 nm, from about 150 nm to about 350 nm, from about 150 nm to about 300 nm, from about 150 nm to about 250 nm, etc). In some embodiments, the first polymer in the composition may have a Rg from about 30 nm to about 500 nm. In some embodiments, the first polymer in the composition may have a Rg from about 150 nm to about 250 nm.

The second polymer in the composition may have a radius of gyration (Rg) less than 100 nm (e.g., from about 1 nm to about 100 nm, from about 3 nm to about 90 nm, from about 3 nm to about 80 nm, from about 3 nm to about 70 nm, from about 3 nm to about 60 nm, from about 3 nm to about 50 nm, from about 3 nm to about 40 nm, from about 3 nm to about 30 nm, from about 3 nm to about 20 nm, from about 5 nm to about 20 nm, etc). In some embodiments, the second polymer in the composition may have a Rg from about 3 nm to about 100 nm. In some embodiments, the second polymer in the composition may have a Rg from about 5 nm to about 20 nm.

In some embodiments, a radius of gyration (Rg) ratio between said first polymer and said second polymer in said composition may be from about 150:1 to about 1:1 (e.g., from about 150:1 to about 1:1, from about 100:1 to about 1:1, from about 80:1 to about 1:1, from about 60:1 to about 1:1, from about 50:1 to about 1:1, from about 30:1 to about 1:1, from about 30:1 to about 5:1, from about 30:1 to about 10:1, etc.). In some embodiments, a radius of gyration (Rg) ratio between said first polymer and said second polymer in said composition may be more than 1:1 (e.g., from about 150:1 to about 1.1:1, from about 100:1 to about 1.1:1, from about 80:1 to about 1.1:1, from about 60:1 to about 1.1:1, from about 50:1 to about 1.1:1, from about 30:1 to about 1.1:1, from about 30:1 to about 5:1, from about 30:1 to about 10:1, etc.). For example, a radius of gyration (Rg) ratio between said first polymer and said second polymer in said composition may be from about 30:1 to about 10:1.

In some embodiments, a molar ratio between said first polymer and said second polymer in said composition may be from about 4:1 to about 1:500 (e.g., from about 4:1 to about 1:500, from about 3:1 to about 1:500, from about 2:1 to about 1:500, from about 1:1 to about 1:500, from about 4:1 to about 1:400, from about 4:1 to about 4:300, from about 4:1 to about 4:200, from about 4:1 to about 1:100, from about 3:1 to about 1:400, from about 2:1 to about 1:300, from about 1:1 to about 1:200, from about 1:1 to about 1:100, from about 1:1 to about 1:500, etc.). For example, a molar ratio between said first polymer and said second polymer in said composition may be from about 1:1 to about 1:50.

In some embodiments, the derivative may have an average degree of modification (DM) of about 3% to about 50% (e.g., about 4% to about 45%, about 5% to about 40%, about 6% to about 40%, about 7% to about 40%, about 8% to about 39%, about 8% to about 38%, about 8% to about 35%, about 9% to about 32%, about 8% to about 30%, about 10% to about 30%, about 12% to about 30%, about 13% to about 30%, about 14% to about 30%, about 15% to about 35%, or about 15% to about 30%).

In some cases, the first polymer derivative may be modified with one or more vinylsulfone groups and the second polymer derivative may be modified with one or more thiol groups. The first polymer derivative may be able to react with the second polymer derivative to form the hydrogel.

In the present disclosure, the first polymer derivative may be a dextran derivative modified with one or more vinylsulfone groups, a hyaluronic acid derivative modified with one or more vinylsulfone groups, a dextran derivative modified with one or more maleimide groups, a hyaluronic acid derivative modified with one or more maleimide groups, a dextran derivative modified with one or more acrylate groups, a hyaluronic acid derivative modified with one or more acrylate groups, a dextran derivative modified with one or more methacrylate groups, a hyaluronic acid derivative modified with one or more methacrylate groups, or a combination thereof. For example, the first polymer derivative may be a dextran derivative modified with one or more vinylsulfone groups, a hyaluronic acid derivative modified with one or more vinylsulfone groups or a hyaluronic acid derivative modified with one or more maleimide groups.

In the present disclosure, the second polymer derivative may be a dextran derivative modified with one or more thiol groups, a hyaluronic acid derivative modified with one or more thiol groups, a dextran derivative modified with one or more amine groups, a hyaluronic acid derivative modified with one or more amine groups, or a combination thereof. For example, the second polymer derivative may be a dextran derivative modified with one or more thiol groups, a hyaluronic acid derivative modified with one or more thiol groups.

In the present disclosure, the first polymer derivative may be a dextran derivative modified with one or more vinylsulfone groups, a hyaluronic acid derivative modified with one or more vinylsulfone groups, a dextran derivative modified with one or more maleimide groups, a hyaluronic acid derivative modified with one or more maleimide groups, a dextran derivative modified with one or more acrylate groups, a hyaluronic acid derivative modified with one or more acrylate groups, a dextran derivative modified with one or more methacrylate groups, a hyaluronic acid derivative modified with one or more methacrylate groups, or a combination thereof, and the second polymer derivative may be a dextran derivative modified with one or more thiol groups, a hyaluronic acid derivative modified with one or more thiol groups, a dextran derivative modified with one or more amine groups, a hyaluronic acid derivative modified with one or more amine groups, or a combination thereof. In some cases, the first polymer derivative may be a dextran derivative modified with one or more vinylsulfone groups, a hyaluronic acid derivative modified with one or more vinylsulfone groups and the second polymer derivative may be a dextran derivative modified with one or more thiol groups, a hyaluronic acid derivative modified with one or more thiol groups. The first polymer derivative may be able to react with the second polymer derivative to form the hydrogel.

For example, the first polymer derivative may comprise a hyaluronic acid derivative modified with one or more vinylsulfone groups (HA-VS) and the second polymer derivative may comprise a hyaluronic acid derivative modified with one or more thiol groups (HA-SH). For another example, the first polymer derivative may be a hyaluronic acid derivative modified with one or more vinylsulfone groups (HA-VS) and the second polymer derivative may be a dextran derivative modified with one or more thiol groups (Dextran-SH). For another example, the first polymer derivative may be a hyaluronic acid derivative modified with one or more maleimide groups (HA-MI) and the second polymer derivative may be a hyaluronic acid derivative modified with one or more thiol groups (HA-SH). The first polymer derivative may be able to react with the second polymer derivative to form polymer-polymer type hydrogel under proper conditions.

In some embodiments, said first polymer may be comprised in said composition in a hydrogel formed. In some embodiments, said second polymer may be comprised in said composition in a hydrogel formed.

In some embodiments, said composition may not comprise any crosslinker different from said one or more polymers.

In some embodiments, the composition may comprise a buffer. The buffer may be an aqueous solution, and may comprise water and appropriate salts useful for adjusting the pH or buffering capacity of the aqueous solution.

The polymer in the composition of the present disclosure may have excellent stability for a long-term storage. The polymer of the present disclosure may not degrade for a long-term storage. The polymer of the present disclosure may not crosslink or form aggregate with itself for a long-term storage. The polymer of the present disclosure may have a stable range of molecular weight.

In another aspect, the present disclosure provides a hydrogel formed with the composition of the present disclosure. In some embodiments, said hydrogel of the present disclosure may be biocompatible.

In some cases, almost all the polymers in the composition may be capable of forming the hydrogel, in some cases, the composition may not comprise any crosslinker different from the one or more polymers.

The hydrogel according to the present disclosure may have one or more specific characteristics/properties.

The hydrogel of the present disclosure may have a storage modulus G' that is no more than 5 Pa (e.g., no more than 4 Pa, no more than 3.5 Pa, no more than 3 Pa, no more than 2.5 Pa, at least 2.4 Pa, at least 2.2 Pa, at least 2 Pa, at least 1.8 Pa, no more than 1.6 Pa, no more than 1.5 Pa, no more than 1.4 Pa, no more than 1.2 Pa, no more than 1.0 Pa, no more than 0.8 Pa, no more than 0.7 Pa, no more than 0.6 Pa, no more than 0.5 Pa, no more than 0.4 Pa, no more than 0.3 Pa, no more than 0.2 Pa, no more than 0.1 Pa, or less), as measured in a dynamic oscillatory shear test at 5% strain and 5 rad/s frequency.

The hydrogel of the present disclosure may have a viscosity that is no more than about 100 mPa·s as measured in a continuous shear test at a frequency shear rate of more than about 1000/s. The hydrogel of the present disclosure may have a viscosity that is at least about 500 mPa·s as measured in a continuous shear test at a frequency shear rate of more than about 0.1/s. The shear viscosity at 0.1/s is at least 10 times higher than the shear viscosity at 1000/s.

The hydrogel of the present disclosure may have a loss modulus G" that is no more than about 100% (e.g., no more than about 90%, no more than about 80%, no more than about 70%, no more than about 60%, no more than about 55%, no more than about 50%, no more than about 45%, no more than about 40%, no more than about 35%, no more than about 30%, no more than about 25%, or no more than about 20%) of its storage modulus G', as measured in a dynamic oscillatory shear test at 5% strain and 5 rad/s frequency.

In some embodiments, the composition may have a pH of about 6.0 to about 8.0 (e.g., about 6.1 to about 7.9, about 6.2 to about 7.7, about 6.3 to about 7.7, about 6.4 to about 7.4, about 6.5 to about 7.3, about 6.6 to about 7.2, about 6.7 to about 7.1, about 6.8 to about 7, about 6.3 to about 6.8, about 6.3 to about 6.7, or about 6.4 to about 6.6).

A rheometer may be used to measure the storage modulus, loss modulus and may be used in a dynamic oscillatory shear test. In another example, a rheometer may comprise a displacement sensor (such as a linear variable differential transformer), which may measure a change in voltage as a result of the instrument probe moving through a magnetic core. The rheometer may further comprise a temperature control system or furnace, a drive motor (e.g., a linear motor for probe loading which may provide load for the applied force), a drive shaft support and a guidance system to act as a guide for the force from the motor to the sample, and one or more sample clamps in order to hold the sample being tested.

Different types of rheometer analyzers may be used. For example, a forced resonance analyzer or a free resonance analyzer may be used. A free resonance analyzer may measure the free oscillations of damping of a sample being tested by suspending and swinging the sample. A forced resonance analyzer may force the sample to oscillate at a certain frequency and may be reliable for performing a temperature sweep. The analyzers may be made for both stress (force) and strain (displacement) control. For example, in strain control, the probe may be displaced and the resulting stress of the sample may be measured by implementing a force balance transducer, which may utilize different shafts. In stress control, a set force may be applied and the resulting strain or displacement of the sample may be measured, and several other experimental conditions (temperature, frequency, or time) may be varied. The stress and strain may be applied via torsional or axial analyzers. With a torsional analyzer, the force is applied in a twisting motion. An axial analyzer may be used for flexure, tensile, and/or compression testing.

A variety of test modes may be employed to probe the viscoelastic properties of polymers and hydrogels, such as temperature sweep testing, frequency sweep testing, strain sweep testing, step stress testing, dynamic stress-strain testing, continuous shear testing, or a combination thereof.

A variety of mechanical properties can be determined by the rheometer. These properties include storage modulus (G'), loss modulus (G"), complex modulus (G*), loss angle (tan (δ)), complex viscosity (η*), it's in phase (η') and out of phase component (η"), complex compliance (J*), storage compliance (J'), loss compliance (J"), viscosity (η) etc.

For example, in the dynamic oscillatory shear test, a sinusoidal force (e.g., a stress) may be applied to a material and the resulting displacement (strain) may be measured. For a perfectly elastic solid, the resulting strain and the stress may be perfectly in phase. For a purely viscous fluid, there may be a 90 degree phase lag of strain with respect to stress. Viscoelastic polymers or hydrogels having characteristics in between may have a phase lag during the test, and the storage and loss modulus may be calculated accordingly.

In another aspect, the present disclosure provides a method for generating a hydrogel (e.g., a hydrogel of the present disclosure). The method may comprise a) providing a composition (e.g., a composition comprising one or more polymers of the present disclosure); and b) subjecting the composition to conditions enabling formation of the hydrogel (e.g., enabling crosslinking of the polymer to form the hydrogel). For example, the conditions may comprise incubating the composition at about 15° C. to about 50° C.

In some cases, the method may comprise cross-linking the polymers in the solution to generate the hydrogel. For example, the conditions enabling formation of the hydrogel may also enable cross-linking of the polymers in the solution.

For example, the method may comprise: 1) preparing a first polymer (or a first polymer derivative) and a second polymer (or a second polymer derivative) (e.g., the first polymer may comprise hyaluronic acids modified with one or more vinylsulfone groups; and the second polymer may comprise hyaluronic acids, dextran or polyethylene glycolmodified with one or more thiol groups) in water, adjusting the pH (for example, by adding a buffer solution); 2) mixing polymers of the first polymer with those of the second polymer at a pre-set ratio, the concentration of the polymers in the composition is as defined in the present disclosure; and 3) incubate the mixture under conditions allowing formation of the hydrogel according to the present disclosure.

In some embodiments, the composition may not comprise any crosslinker different from the polymers (e.g., the first polymer derivative, or the second polymer derivate) in the composition.

In some embodiments, the composition may not comprise any small molecule crosslinker.

In a specific example, the first polymer derivative is a hyaluronic acid modified with one or more vinylsulfone groups (e.g., HA-VS), and the second polymer derivative is a hyaluronic acid or dextran modified with one or more thiol groups (e.g., HA-SH or Dextran-SH).

In another aspect, the present disclosure provides a pharmaceutical composition, which comprises the hydrogel. The pharmaceutical composition may further comprise pharmaceutically acceptable adjuvant, pharmaceutical drugs, and/or diagnostic compounds. Suitable pharmaceutically acceptable adjuvant, pharmaceutical drugs and/or diagnostic compounds may be water soluble, water sparely soluble and insoluble pharmaceutical compounds. The pharmaceutical composition may be in any form. Suitable forms will be dependent, in part, of the intended mode and location of application.

In the present disclosure, the composition, the hydrogel and/or the pharmaceutical composition may further comprise a bioactive agent (e.g., an active pharmaceutical ingredient or a drug), and the bioactive agent is encapsulated in the composition, the hydrogel and/or the pharmaceutical composition. The bioactive agent may be a small molecule, a protein, a peptide, an oligonucleotide, an aptamer, or a nucleic acids. For example, the bioactive agent may be an antibacterial agent, anti-fungal agent, anti-viral agent, anti-inflammatory agent, Immunosuppressant, antibiotic, antibody, an angiogenesis inhibitor. For example, the bioactive agent may be suitable for using in eye disease or condition. The bioactive agent may be cumulatively released from the hydrogel in more than 3 days, 3 days, 2 days, 1 day, 12 hours, 8 hours, 4 hours, 3 hours, 2 hours, 1 hour, or less.

EXAMPLES

The following examples are set forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); nt, nucleotide(s); i.m., intramuscular(ly); i.p., intraperitoneal(ly); s.c., subcutaneous(ly); and the like.

Example 1 Measurement of Rg and [η]

Rg and [η] of a polymer can be measured directly, for example by hydrogel permeation chromatography coupled with a multiangle laser light scattering (MALL) detector and a capillary viscometer. The Rg and [η] of many polymers has been measured, for example in hyaluronic acids (HA) (Mendichi R, et al., Evaluation of radius of gyration and intrinsic viscosity molar mass dependence and stiffness of hyaluronan. Biomacromolecules. 2003; 4(6):1805-1810), dextran (Joan, C. E. et al., Structure properties of dextran. 2. dilute solution. Macromolecules, 2000; 33(15), 5730-5739. Or Kasaai M. R., Dilute solution properties and degree of chain branching for dextran, Carbohydrate Polymers 88 (2012) 373-381), carboxymethyl cellulose (Hoogendam, C. W. et al., Persistence length of carboxymethyl cellulose as evaluated from size exclusion chromatography and potentiometric titrations. Macromolecules, 1998:31(18), 6297-6309. Or Sitaramaiah and Gorning, Hydrodynamic Studies on Sodium Carboxymethyl Cellulose iFFIGn Aqueous Solutions, Journal of Polymer Science, 1962; (58) 1107-1131. Or E. Arinaitwe, M. Pawlik, Dilute solution properties of carboxymethyl celluloses of various molecular weights and degrees of substitution, Carbohydrate Polymers 99 (2014) 423-431), and polyethylene glycol (Devanand K, Selser J C. Asymptotic behavior and long-range interactions in aqueous solutions of poly(ethylene oxide). Macromolecules. 1991; 24(22):5943-5947. Or Wu, X. et al., Viscoelasticity of poly(ethylene glycol) in aqueous solutions of potassium sulfate: a comparison of quartz crystal microbalance with conventional methods. Polymer Journal, 2019: doi:10.1038/s41428-018-0162-3).

Some of the Rg and [η] value is given in Table 1,2 and 3.

TABLE 1

Rg and [η] value for polymers of 500 KDa MW

| Polymer | HA | dextran | carboxymethyl cellulose | polyethylene glycol |
|---|---|---|---|---|
| Rg (nm) | ~75 | ~20 | ~70 | ~45 |
| [η] (ml/g) | ~1000 | 50 | ~1800 | 300 |

TABLE 2

Rg and [η] value for HA of different MW

| MW (kDa) | 10 | 29 | 65 | 120 | 670 | 2600 |
|---|---|---|---|---|---|---|
| Rg (nm) | 6.7 | 12.6 | 20.3 | 29.3 | 81.6 | 183 |
| [η] (ml/g) | 21.6 | 66.5 | 106 | 303 | 1156 | 2960 |

TABLE 3

| Rg and [η] value for dextran of different MW | | | |
|---|---|---|---|
| MW (kDa) | 40 | 70 | 150 |
| Rg (nm) | 6.2 | 8 | ~10 |
| [η] (ml/g) | 18.9 | 25.2 | 37 |

Example 2 Preparation of Polymer Derivatives 2.1 The Preparation of HA-VS

Hyaluronic acids (HA) were modified with pedant VS as described by Yu and Chau (Biomacromolecules 2015, 16 (1), 56-65) (FIG. 1). Briefly, HA was dissolved in deionized water (DI water). The concentration was from 0.1 mg/ml to 40 mg/ml depending on molecular weight (MW) of HA. For high MW HA (e.g. MW>1 MDa), the concentration was lower, for low MW HA (e.g., MW<100 kDa), the concentration was higher.

After complete dissolution, 5M NaOH was added drop wise to the polymer solution to a final concentration at 0.1M. Divinylsulfone (DVS) was added instantly with vigorous mixing. The molar ratio between DVS and hydroxyl groups (OH) of HA was at least 1.25:1. The DVS concentration and reaction time was chosen depending on the target degree of modification (DM). For a given reaction time, the degree of modification was also depending on the concentration of both HA and DVS, the temperature and the final NaOH concentration. The reaction was stopped by adding 1M HCl to reduce the pH to 3.5-4.5. The polymers were purified by membrane separation using dialysis bag or tangential flow filtration against DI water. Unless specified, the purified polymer was stored as a solution at 4° C. For measuring the degree of modification (DM), HA-VS was freeze dried and determined by $^{1}$H NMR.

2.2 The Preparation of HA-SH

Figure 2:
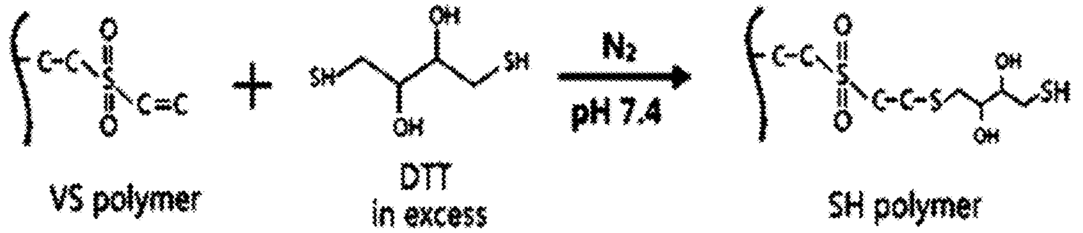
FIG. 2 illustrates the synthesis of HA-SH polymer.

Hyaluronic acids (HA) were modified with pedant thiol (SH) group as described by Yu and Chau (Biomacromolecules 2015, 16 (1), 56-65) (FIG. 2). Briefly, HA was first modified to HA-VS (as described in Example 2.1). The HA-VS solution was purged with $N_2$ for at least 20 minutes. Dithiothreitol (DTT) of 10× molar excess to vinyl sulfone (VS) group or the amount needed to make a 0.05M DTT solution (depending on which DTT concentration is higher) was dissolved in water (pH about 5.5) at about 400 mg/ml and purged with $N_2$ for at least 5 minutes and added to the HA-VS solution. The pH of the HA-VS/DTT solution was around 4 and the system was continued to be purged with $N_2$. Afterwards, 0.5M phosphate buffer (PB) of 1/10 the volume of HA-VS was purged with $N_2$ for at least 5 minutes and added to the HA-VS/DTT solution. The reaction was allowed for at least 25 minutes. The reaction was stopped by adding 1M HCl to reduce the pH to 3.5-4.5. The polymers were purified by membrane separation using dialysis bag or tangential flow filtration against DI water of pH 4 adjusted by HCl. Unless specified, the purified polymer was stored as a solution at 4° C. The degree of modification (DM) was determined by Ellmans' assay for HA-SH.

2.3 The Preparation of Dextran-SH

The vinyl sulfone (VS) and thiol (SH) functionalized dextran, Dextran-VS and Dextran-SH were synthesized using previously reported method (refers to Y. Yu and Y. Chau, "One-step 'click' method for generating vinyl sulfone groups on hydroxyl-containing water-soluble polymers," Biomacromolecules, vol. 13, pp. 937-942, 2012). In brief, divinylsulfone (DVS) reacts with hydroxyl groups on dextran in aqueous, alkaline condition to make Dextran-VS (FIG. 1). Thiol functionalized dextran using dithiothreitol (DTT) to react with the VS groups on Dextran-VS in phosphate buffered solution to make Dextran-SH (FIG. 2), the functionalization protocol is similar to Example 2.2. The polymers were purified by membrane separation using dialysis bag or tangential flow filtration against DI water of pH 4 adjusted by HCl. Unless specified, the purified polymer was stored as a solution at 4° C. DM of Dextran-VS was determined using $^{1}$H NMR, and DM of Dextran-SH was determined by Ellman's assay.

Example 3 Stability of Modified Polymer of High Intrinsic Viscosity [η]

HA-SH and HA-VS was modified according to Example 2.2 and 2.1. To illustrate the stability of high molecular weight HA, these HA derivatives were modified from HA of 2.6 MDa ([η]=2960 ml/g, Rg=183 nm) molecular weight. The stability of the HA-SH was evaluated by agarose hydrogel electrophoresis (AGE) and the stability of the HA-VS was evaluated by gel permeation chromatography (GPC).

The protocol for AGE was modified from a previous report (Lee and Cowman, An agarose gel electrophoretic method for analysis of hyaluronan molecular weight distribution, Analytical Chemistry, 1994:219; 278-287). Briefly, HA-SH samples of about 15% DM in AGE loading buffer were loaded into the agarose gel composed of 5 mg/ml high melting temperature agarose (Solarbio, Beijing, China) in TEA buffer. After electrophoresis for 1 hour at 80 mV, the hydrogel was stained by 0.005% Stain-All (Sigma) in 50% ethanol overnight. The hydrogel was detained with 10% ethanol.

The GPC condition was listed below:

HPLC: Waters 2695

Differential reflective index detector: Waters 2414

Mobile phase: 0.2M NaCl and 0.01% sodium azide solution

Flow rate: 0.5 mL/min

Column: Ultrahydrogel Linear, 7.8×300 mm, WAT011545, 005C181201, No. KNC-COL-003.

The temperature of column thermostat was 35° C., the temperature of detector was 30° C.

Figure 4A:
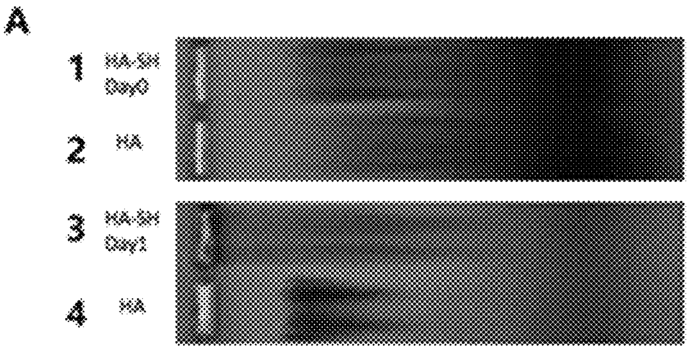
FIG. 4A illustrates the change of MW as measured by agarose hydrogel electrophoresis (AGE) of HA-SH after reaction and after 1 day dialysis as a solution at about 1 mg/ml against pH 4 HCl.
Figure 4B:
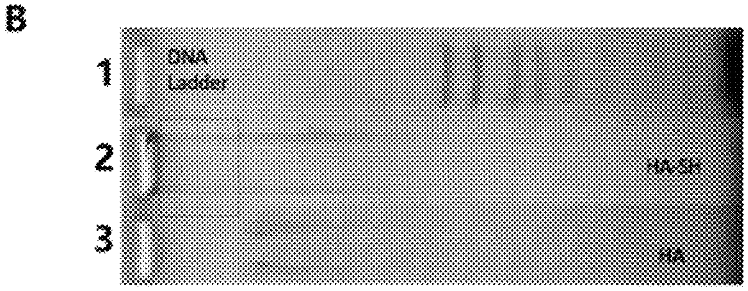
FIG. 4B illustrates the distribution MW as measured by AGE of HA and HA-SH.

The results of FIG. 4A-4B showed that the HA-SH derived from 2.6 MDa HA (with an intrinsic viscosity of more than 1800 ml/g) was not stable as a solution. Lane 2 and 4 of FIG. 4A shows the AGE result of unmodified HA, and Lane 1 and 3 of FIG. 4A shows the AGE result of HA-SH right after reaction and after 1 day dialysis as a solution at about 1 mg/ml against pH 4 deionized water (pH adjusted with HCl). The result showed that the molecular weight of HA-SH was normal after reaction, but after 1 day dialysis in acidic condition, the MW of HA-SH increased as evidence from the appearance of smear closed to the well of lane 3. Lane 2 and 3 of FIG. 4B shows another AGE result of HA-SH and unmodified HA respectively.

In addition, if HA-SH was lyophilized, the lyophilized powered could not be re-dissolve in solution again and will form a gel.

Figure 5:
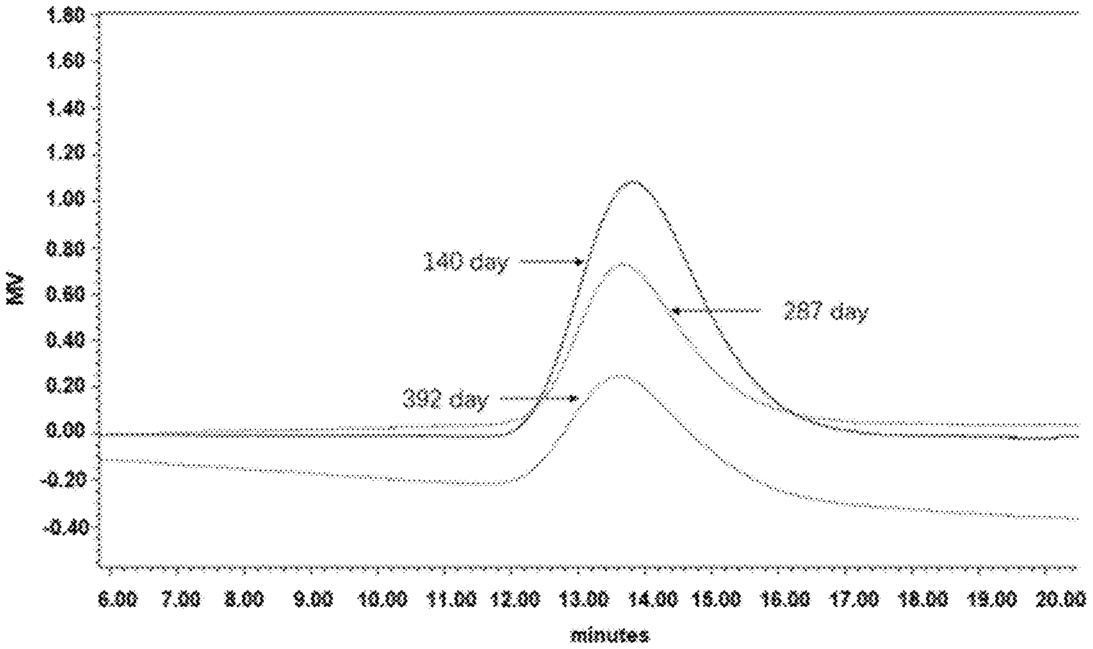
FIG. 5 illustrate examples of GPC curve of HA-VS of 2.6 MDa, 23% DM.

On the contrary, the HA-VS is stable as a solution over a long period of time (FIG. 5).

Example 4 Stability of Modified Polymer of Low Intrinsic Viscosity [η]

The HA-SH and Dextran-SH (i.e., Dex-SH) modified from HA of about 65 kDa ([η]=106 ml/g), 670 kDa ([η]

=1156 ml/g) and dextran of about 45 kDa ([η]=20 ml/g) were used as examples showing the stability of low intrinsic viscosity polymer. The HA-SH was prepared as described in example 2.2. The Dex-SH was prepared as described in example 2.3. The molecular weight stability of the samples were evaluated by GPC and the testing method was described in example 3.

The molecular weight (MW) and poly dispersity (PDI) of the polymer was estimated by comparing to a universal calibration curve generated from poly(styrene sulfonate) sodium salt polymer standard.

The polymers are stored as a solution at pH 3 at 4° C.

Example 4.1 Stability of HA-SH of 15% DM and 65 kDa

The results of HA-SH of 15% DM were shown in Table 4.

TABLE 4

The molecular weight of HA-SH over a period of time

| Day | MW (Da, mean ± SD/PDI ± SD) |
|---|---|
| 0 day | 69280/1.29 |
| 6 day | 63589/1.28 |
| 12 day | 64432/1.32 |
| 18 day | 65972 ± 1182/ 1.345 ± 0.021 |
| 22 day | 65312 ± 180/ 1.334 ± 0.004 |
| 27 day | 65396 ± 315/ 1.343 ± 0.006 |
| 36 day | 68432 ± 412/ 1.371 ± 0.044 |
| 67 day | 62335 ± 1700/ 1.364 ± 0.004 |
| 97 day | 70355 ± 423/ 1.379 ± 0.007 |
| 130 day | 71966 ± 1131/ 1.411 ± 0.030 |

Figure 6A:
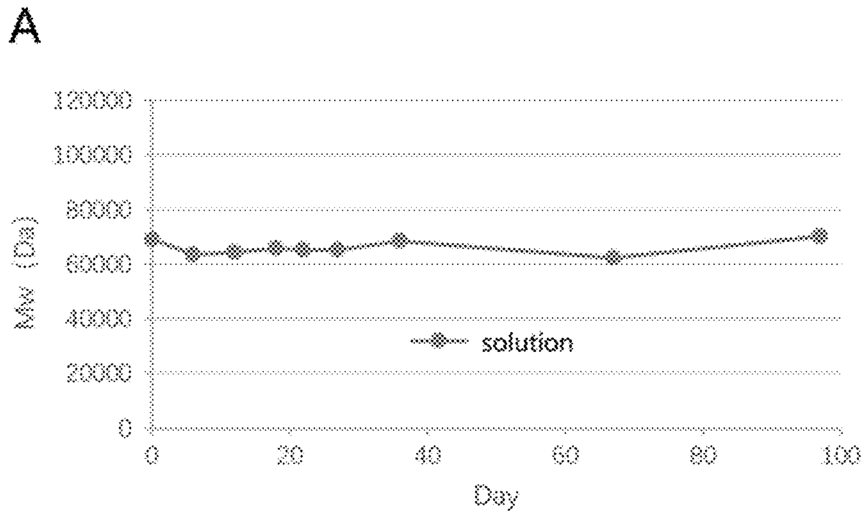
FIGS. 6A and 6B illustrate the change of MW (6A) of HA-SH as a solution at 4° C. and example of the hydrogel permeation chromatography (GPC) curve (6B) of HA-SH stored as a solution at 4° C.
Figure 6B:
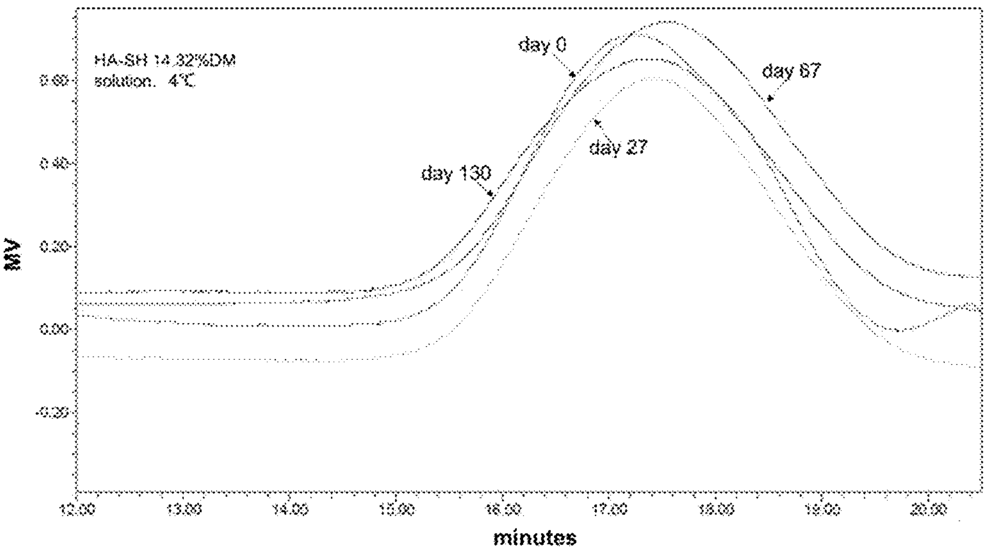

Surprisingly, although the storage condition for HA-SH in solution form is similar to Example 3, from Table 4 we can see that, the HA-SH with a lower intrinsic viscosity was stable as a solution for at least 60 days. And only a slight increase in MW was seen after about 90 days. FIG. 6 showed the trend of MW change and examples of the original GPS curve of the polymers of Table 4.

Example 4.2 Stability of HA-SH of 25% DM and 65 kDa

Example 4.1 shows surprisingly stable SH polymer in solution just by modifying a low [η] polymer, we further investigated if SH polymer of higher DM in solution (10.16 mg/mL) at 4° C. can be stable.

TABLE 5

The molecular weight of HA-SH over a period of time

| Day | MW (Da, mean ± SD/PDI ± SD) |
|---|---|
| 0 day | 62313/1.33 |
| 9 day | 61009/1.29 |
| 15 day | 63038/1.33 |
| 21 day | 65732 ± 371/ 1.353 ± 0.009 |
| 25 day | 66660 ± 303/ 1.377 ± 0.006 |
| 30 day | 67631 ± 965/ 1.396 ± 0.016 |
| 39 day | 66091 ± 4021/ 1.397 ± 0.027 |
| 70 day | 65093 ± 1518/ 1.431 ± 0.011 |

Figure 7A:
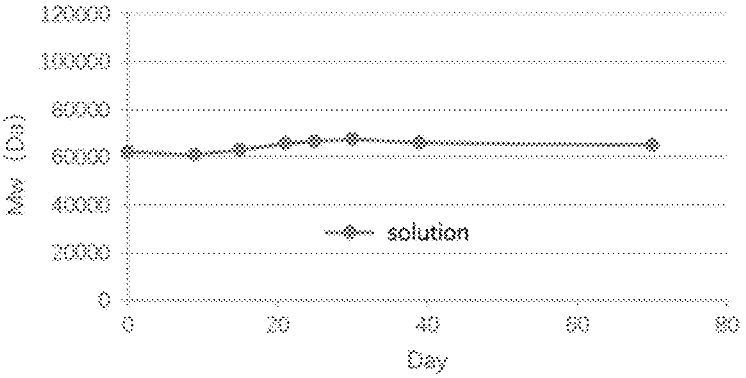
FIGS. 7A and 7B illustrate the change of MW (7A) of HA-SH as a solution at 4° C. and example of the GPC curve (7B) of HA-SH stored as a solution at 4° C.
Figure 7B:
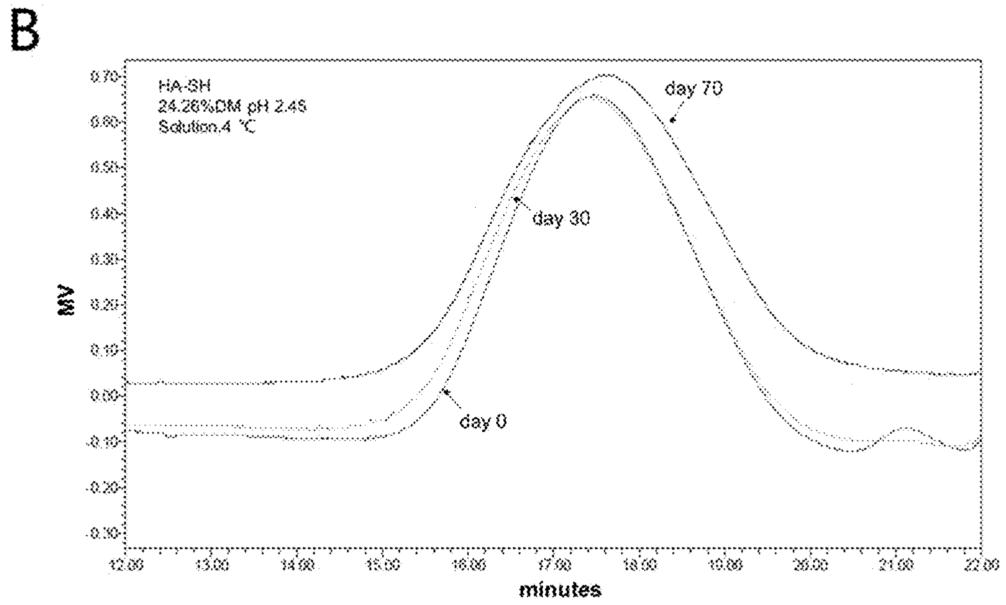
Figure 8A:
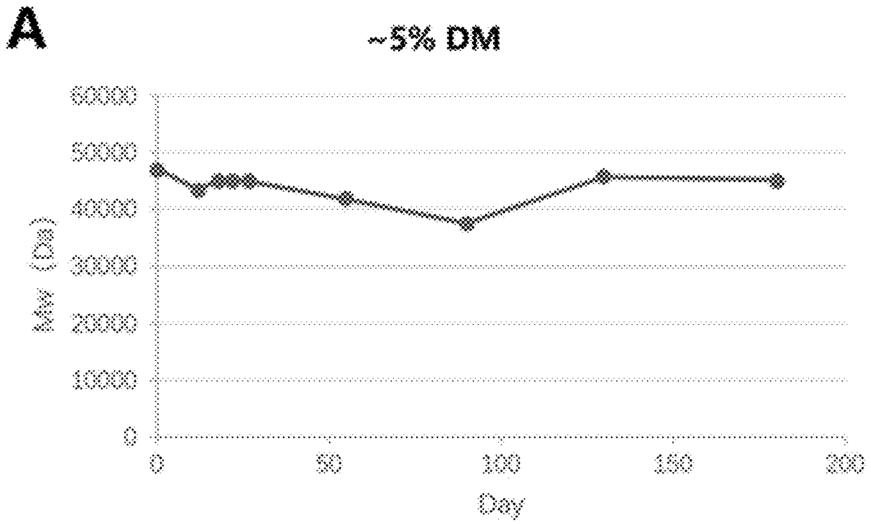
FIGS. 8A, 8B, 8C and 8D illustrates the change of MW (8A) and example of GPC curve (8B) of Dextran-SH of 5% DM, and the change of MW (8C) and example of GPC curve (8D) of Dextran-SH of 12.5% DM.
Figure 8B:
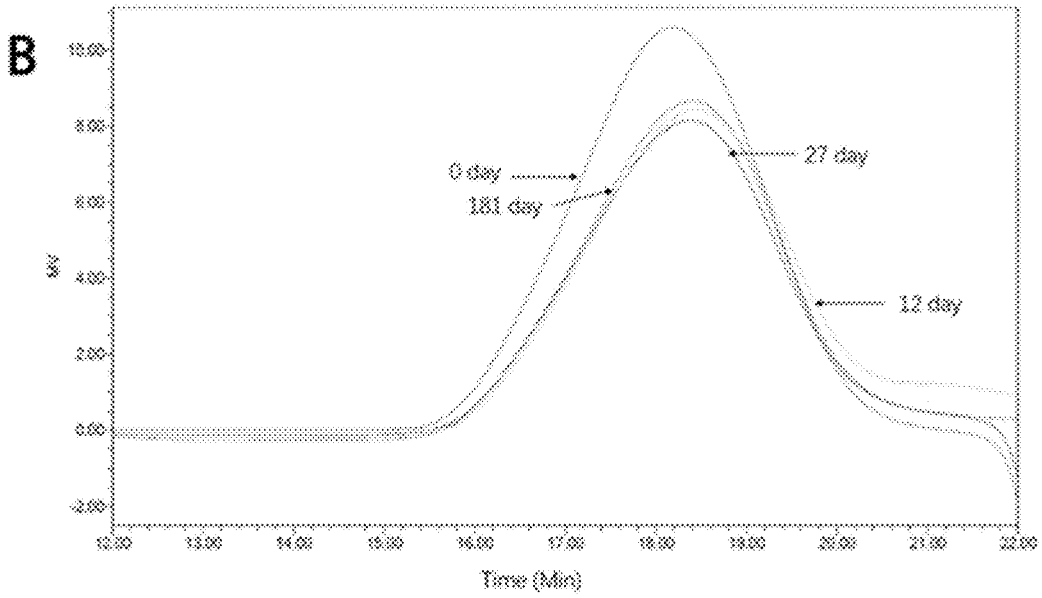
Figure 8C:
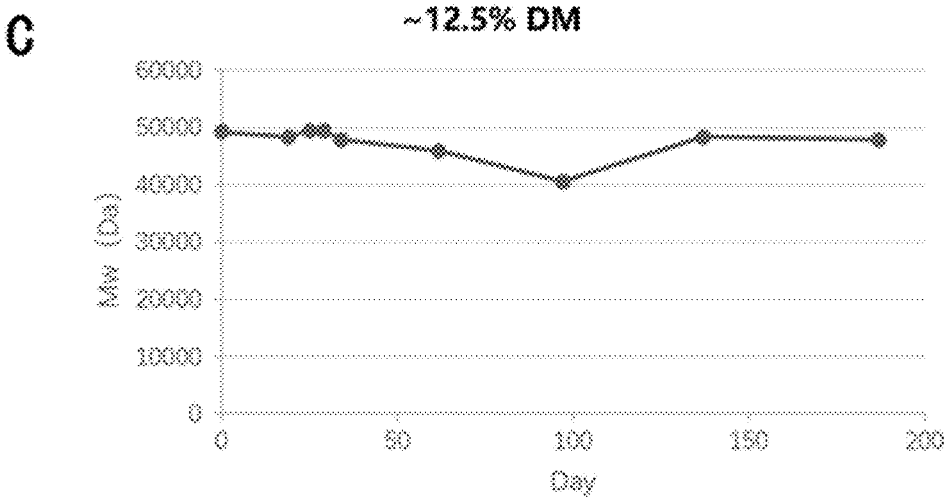
Figure 8D:
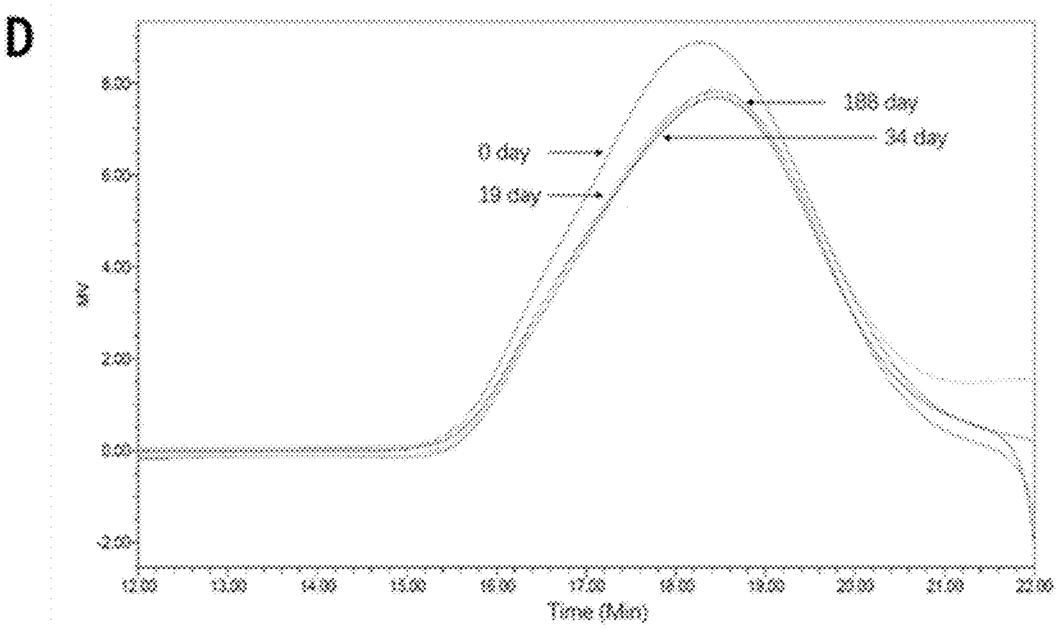

Table 5 showed an example of stability of 65 kDa HA-SH of 25% DM. The result showed that the MW of HA-SH was stable for at least 70 days. FIG. 7 showed the trend of MW change and examples of the original GPS curve of the polymers of Table 5.

Example 4.3 Stability of Dextran-SH 45 kDa of about 5% and 12.5% DM

To further demonstrate the stability of SH polymer having low [η], dextran of about 45 kDa was modified to Dextran-SH according to Example 2. Two DM of Dextran-SH, 5% and 12.5%, was used as examples. It should be noted that, the dextran is a polymer composed of monosaccharides repeat and the MW of the repeating unit is about 160 Da, compares to disaccharides repeat of HA, which has a MW of about 400 Da. For this reason, 5% and 12.5% DM of Dextran-SH has a similar SH density to HA-SH of 12% and 30% DM accordingly.

The result of the study was shown in table 6. It was found that both polymer's MW did not increase for at least 180 days. FIG. 8 showed the trend of MW change and examples of the original GPS curve of the polymers of Table 6.

TABLE 6

The molecular weight of Dextran-SH over a period of time

| Dextran-SH, 5% DM, 16.5 mg/mL | | Dextran-SH, 12.5% DM, 14.5 mg/mL | |
|---|---|---|---|
| Day | MW (Da, mean ± SD/PDI ± SD) | Day | MW (Da, mean ± SD/PDI ± SD) |
| 0 day | 47089/1.361 | 0 day | 49240/1.458 |
| 12 day | 43399 ± 448/ 1.367 ± 0.009 | 19 day | 48309 ± 225/ 1.477 ± 0.009 |
| 18 day | 45139 ± 447/ 1.378 ± 0.002 | 25 day | 49459 ± 182/ 1.470 ± 0.002 |
| 22 day | 45139 ± 447/ 1.378 ± 0.002 | 29 day | 49459 ± 182/ 1.470 ± 0.002 |
| 27 day | 44939 ± 264/ 1.362 ± 0.005 | 34 day | 47867 ± 100/ 1.450 ± 0.001 |
| 55 day | 41763 ± 370/ 1.380 ± 0.004 | 62 day | 45944 ± 356/ 1.454 ± 0.010 |
| 90 day | 37494 ± 215/ 1.366 ± 0.004 | 97 day | 40617 ± 454/ 1.418 ± 0.005 |
| 130 day | 45663 ± 87/ 1.368 ± 0.003 | 137 day | 48305 ± 1101/ 1.450 ± 0.007 |
| 180 day | 45133 ± 75/ 1.378 ± 0.004 | 187 day | 47886 ± 151/ 1.465 ± 0.002 |

4.4 Stability of HA-SH of 16.4% DM and 670 kDa.

We further investigated if a polymer of slightly higher MW and intrinsic viscosity, HA-SH of 670 kDa, [η]=1156 ml/g is stable in solution (5.5 mg/mL) at 4° C. In this example the DM of the polymer was 16.4%.

Figure 13:
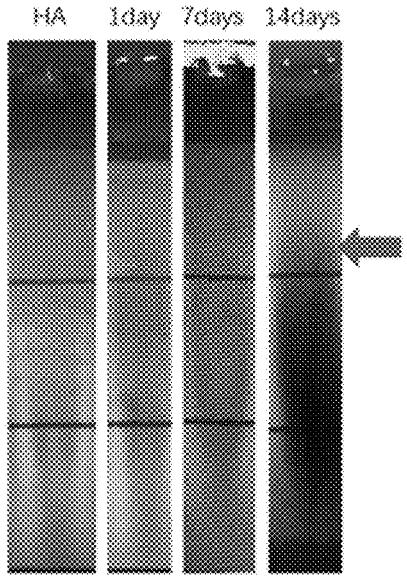
FIG. 13 illustrates the change of MW as measured by AGE of HA-SH of 16.4% DM and 670 kDa at after different incubation period.

The HA-SH was stored in pH 3 dilute HCl solution. We found that the polymer was stable at day 1 after purification. 7 days later, the polymer is still mostly uncrosslink, though some high MW fraction can be seen. At 14 days, polymer of higher MW (as indicated by the arrow) can be seen in AGE. At 30 days, the polymer formed a gel by itself, indicating significant self-crosslinking. The result (FIG. 13) shows that the material is relatively stable compares to 2.6 MDa HA-SH.

Example 5 Formation of Hydrogel by Modified High [η] Polymer and Modified Low [η] Polymer HA-VS, HA-SH and Dextran-SH was made according to Example 2. The concentration of HA-VS and HA-SH or Dextran-SH was first determined. The polymer solution of known volume was freeze dried and the dry weight of polymer was measured. The dry polymer was at least 4 mg to ensure accurate measurement. Alternatively, the polymer concentration of HA-VS and HA-SH were measured by CTAB assay as described previously (Oueslati et al., CTAB turbidimetric method for assaying hyaluronic acid in complex environments and under cross-linked form, Carbohydrate Polymers, 2014), the polymer concentration of Dextran-SH was measured by polarimeter according to China Pharmacopoeia. HA-VS and HA-SH or Dextran-SH of known concentration was then adjusted to pH 7.4 by the addition of 0.5M PB. The final concentration of PB was about 0.02M to 0.05M. The osmolality was then adjusted using 25% NaCl. The polymers were then mixed at various target volume ratio and mass ratio, and adjusted to the target final concentration by adding phosphate buffered saline (PBS).

Figure 3:
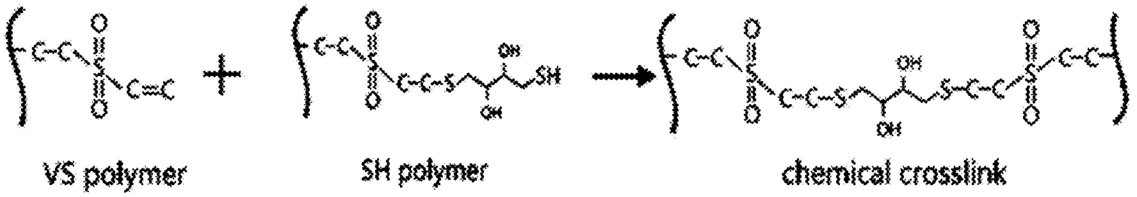
FIG. 3 illustrates the formation of the hydrogel of the present disclosure.

The polymers were incubated at 37° C. for 24 hours for hydrogel formation. The hydrogel formation reaction is demonstrated in FIG. 3. After the incubation period, the hydrogel was first checked for gel formation visually with the help of careful pipettement. For those conditions that successfully forms a gel-like structure, the hydrogel formed was loaded onto the lower plate of a 60 mm cone-plate fixture (CP60-1/T1) of an Anton Paar rheometer, and the mechanical properties (e.g., G' and G") were measured. A higher G' value comparing to G" value (e.g., G'>G") at the linear viscoelastic region (LVR) region was used as an objective indication for hydrogel formation.

5.1 Hydrogels Formed by Polymers with Varied Concentrations

As a demonstration of principle, a large [η] polymer (HA-VS of 2.6 MDa at 23% DM, [η]=2960 ml/g) was mixed a with small [η] polymer (HA-SH of 65 kDa at 14% DM, [η]=106 ml/g) as following:

Group 1: HA-SH at 0.64 mg/ml, and HA-VS at 1.01 mg/ml, 0.81 mg/ml, 0.65 mg/ml, 0.52 mg/ml, 0.42 mg/ml, 0.33 mg/ml, respectively.

Group 2: HA-SH at 0.43 mg/ml, and HA-VS at 1.01 mg/ml, 0.81 mg/ml, 0.65 mg/ml, 0.52 mg/ml, 0.42 mg/ml, 0.33 mg/ml, respectively.

Group 3: HA-SH at 0.34 mg/ml, and HA-VS at 1.27 mg/ml, 1.01 mg/ml, 0.81 mg/ml, 0.65 mg/ml, 0.52 mg/ml, 0.41 mg/ml, respectively.

Group 4: HA-SH at 0.28 mg/ml, and HA-VS at 1.27 mg/ml, 1.01 mg/ml, 0.81 mg/ml, 0.65 mg/ml, 0.52 mg/ml, 0.41 mg/ml, respectively.

Figure 9:
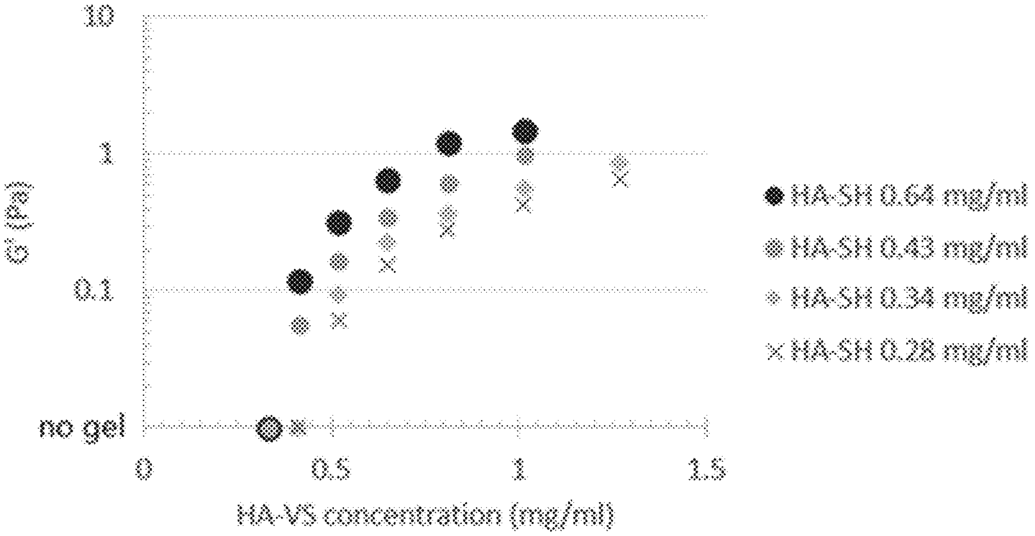
FIG. 9 illustrates the trend in the change of G' of gels at different HA-SH concentrations.
Figure 10:
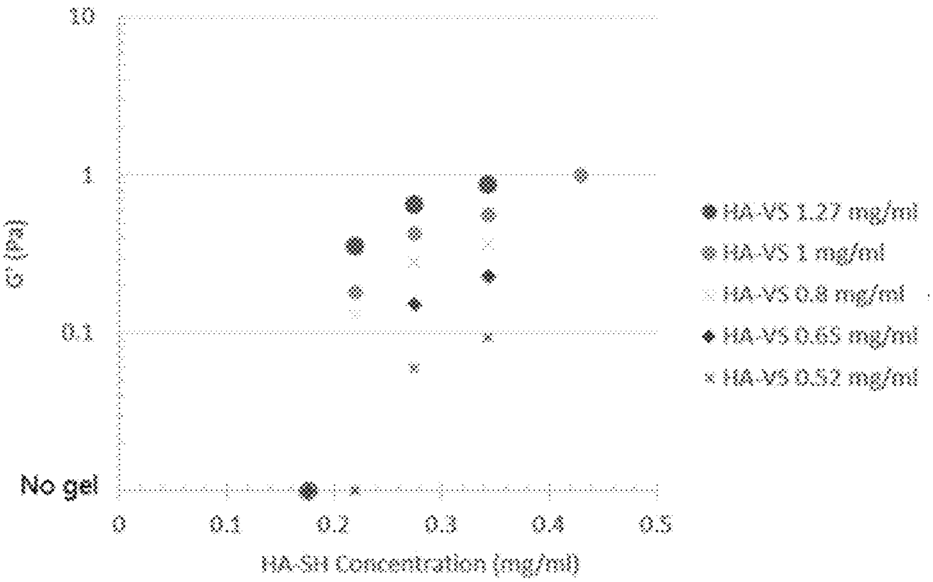
FIG. 10 illustrates the trend in the change of G' of gels at different HA-VS concentrations.

The G' and G" (n=3 for each formulation) measured at 5 rad/s frequency and 5% strain were shown in Table 7-10. The FIGS. 9-10 showed the trend in the change of G' of different formulations. These results showed if the HA-VS concentration was kept constant, the mechanical properties would decrease as the HA-SH concentration decreased. If the HA-SH was kept constant, the mechanical properties would decrease as the HA-VS concentration decreased. G' of desirable value could be adjust by adjusting the two gel forming polymers' concentration. No gel can be formed when the concentration of HA-VS is below its overlapping concentration (c*), or about 0.33 mg/ml. The overlapping concentration can be calculated by:

$$c^*=1/[\eta].$$

TABLE 7

Gel formation of HA-SH 65 kDa 14% DM at 0.64 mg/ml

| HA-VS Conc (mg/ml) | HA-VS:HA-SH molar ratio | G'(Pa) | SD(Pa) | G"(Pa) | SD(Pa) |
|---|---|---|---|---|---|
| 1.01 | 1:25.3 | 1.47309 | 0.001786 | 0.173983 | 0.0011972 |
| 0.81 | 1:31.6 | 1.20246 | 0.0023788 | 0.123693 | 0.001912 |
| 0.65 | 1:39.4 | 0.640481 | 0.0030479 | 0.0954332 | 0.0050211 |
| 0.52 | 1:49.2 | 0.320423 | 0.0016018 | 0.0730462 | 0.005164 |
| 0.42 | 1:61.0 | 0.118567 | 0.0034458 | 0.0502013 | 0.0472064 |
| 0.33 | 1:77.6 | No gel | | | |

TABLE 8

Gel formation of HA-SH 65 kDa 14% DM at 0.34 mg/ml

| HA-VS Conc (mg/ml) | HA-VS:HA-SH molar ratio | G'(Pa) | SD(Pa) | G"(Pa) | SD(Pa) |
|---|---|---|---|---|---|
| 1.27 | 1:13.5 | 0.871 | 0.002 | 0.301 | 0.003 |
| 1.01 | 1:17.0 | 0.567 | 0.002 | 0.201 | 0.003 |
| 0.81 | 1:21.2 | 0.365 | 0.003 | 0.140 | 0.002 |
| 0.65 | 1:26.5 | 0.229 | 0.003 | 0.102 | 0.002 |
| 0.52 | 1:33.1 | 0.093 | 0.001 | 0.066 | 0.002 |
| 0.41 | 1:41.0 | No gel | | | |

TABLE 9

Gel formation of HA-SH 65 kDa 14% DM at 0.43 mg/ml

| HA-VS Conc (mg/ml) | HA-VS:HA-SH molar ratio | G'(Pa) | SD(Pa) | G"(Pa) | SD(Pa) |
|---|---|---|---|---|---|
| 1.01 | 1:10.7 | 0.999 | 0.004 | 0.229 | 0.003 |
| 0.81 | 1:13.5 | 0.611 | 0.001 | 0.134 | 0.002 |
| 0.65 | 1:16.8 | 0.346 | 0.002 | 0.107 | 0.002 |
| 0.52 | 1:20.9 | 0.165 | 0.002 | 0.070 | 0.002 |
| 0.42 | 1:26.2 | 0.057 | 0.002 | 0.041 | 0.001 |
| 0.33 | 1:32.4 | No gel | | | |

TABLE 10

Gel formation of HA-SH 65 kDa 14% DM at 0.28 mg/ml

| HA-VS Conc (mg/ml) | HA-VS:HA-SH molar ratio | G'(Pa) | SD(Pa) | G"(Pa) | SD(Pa) |
|---|---|---|---|---|---|
| 1.27 | 1:8.8 | 0.649 | 0.002 | 0.293 | 0.003 |
| 1.01 | 1:11.1 | 0.428 | 0.002 | 0.189 | 0.002 |
| 0.81 | 1:13.8 | 0.281 | 0.002 | 0.134 | 0.002 |
| 0.65 | 1:17.2 | 0.152 | 0.002 | 0.094 | 0.001 |
| 0.52 | 1:21.5 | 0.060 | 0.002 | 0.056 | 0.002 |
| 0.41 | 1:26.7 | No gel | | | |

Another hydrogel was formed by using a large [η] polymer (HA-VS of 2.6 MDa at 23% DM, [η]=2960 ml/g) and mixed with low MW small [η] polymer (HA-SH of 670 kDa at 16.4% DM, prepared as Example 2.2, [η]=1156 ml/g). For the mixture of HA-VS at 0.8 mg/ml and HA-SH at 0.4 mg/ml (The molar ratio between HA-VS and HA-SH was 1:1.9), a hydrogel was formed.

Another hydrogel was formed by using a large [η] polymer (HA-VS of 670 kDa, prepared as Example 2.1, [η]=1156 ml/g) and mixed with low MW small [η] polymer (HA-SH of 65 kDa, prepared as Example 2.2, [η]=106 ml/g). In this example, the concentration of HA-VS was 2.5 mg/ml and the DM was 40%. The concentration of HA-SH was 0.42 mg/ml and the DM was 14.3%. The molar ratio between HA-VS and HA-SH was 1:1.7. At 5% strain and 1 rad/s, the G' was 0.96 Pa and G" was 0.38 Pa. In another example, the concentration of HA-VS was 4 mg/ml and the DM was 40%. The concentration of HA-SH was 0.08 mg/ml and the DM was 14.3%. The molar ratio between HA-VS and HA-SH was 4.9:1. No gel was formed. In another example, the concentration of HA-VS was 4 mg/ml and the DM was 40%. The concentration of HA-SH was 0.16 mg/ml and the DM was 14.3%. The molar ratio between HA-VS and HA-SH was 2.4:1. The mechanical properties of this gel are shown in Table 11.

TABLE 11

| Mechanical properties of Gel | | |
|---|---|---|
| **At 5% strain** | | |
| Frequency | G'(Pa) | G" (Pa) |
| 1 rad/s | 0.69 | 0.51 |
| 5 rad/s | 1.29 | 1.15 |
| 10 rad/s | 1.71 | 1.66 |
| **At 5 rad/s frequency** | | |
| Strain | G'(Pa) | G" (Pa) |
| 1% | 1.2 | 1.15 |
| 10% | 1.28 | 1.14 |
| 100% | 1.08 | 1.11 |
| **Continuous test** | | |
| Strain rate | Viscosity (cP) | |
| 0.1 | 9150 | |
| 1 | 5490 | |
| 10 | 1500 | |
| 120 | 268 | |
| 1000 | 71 | |
| 1250 | 65 | |

5.2 Hydrogels Formed by Polymers with Different DMs

Figure 11:
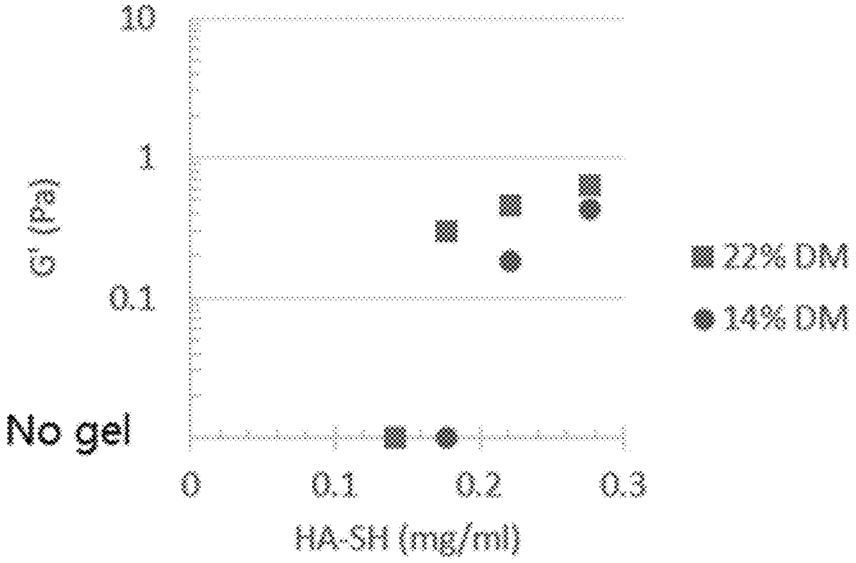
FIG. 11 illustrates the trend in the change of G' of gels at different DM.

The DM of the small [η] polymer can be changed and the hydrogel can be formed. FIG. 11 shows hydrogel's G' value made by mixing HA-VS of 2.6 MDa at 23% DM at 1 mg/ml and HA-SH of 65 kDa at 14% or 22% DM. The value was measured with 5 rad/s frequency and 5% strain. The formulations areas following:

Group 1: HA-SH at 14% DM, and HA-SH from about 0.14 mg/ml to about 0.3 mg/ml, respectively.

Group 2: HA-SH at 22% DM, and HA-SH from about 0.14 mg/ml to about 0.3 mg/ml, respectively. The result (FIG. 11) showed that when the HA-VS was kept constant, that the mechanical strength of hydrogel was lowered when the concentration and DM of HA-SH was reduced. Thus G' desirable value could be adjusted by adjusting DM and concentration of the hydrogel forming polymer.

5.3 Hydrogels formed by Dextran-SH

Figure 12:
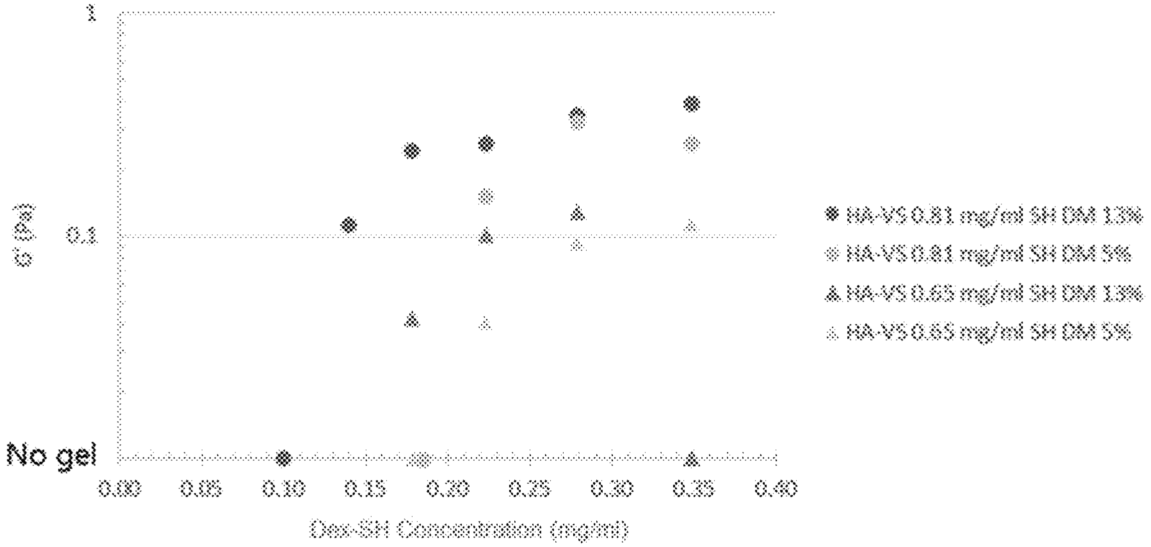
FIG. 12 illustrates the trend in the change of G' of Dextran-SH formed gel.

Another polymer of small [η], Dextran-SH of 45 kDa (or [η]=20 ml/g) was used another example. Table 12 and FIG. 12 showed the G' of different formulations of composed of a large [η] polymer (HA-VS of 2.6 MDa at 23% DM, [η]=2960 ml/g) and Dextran-SH of 45 kDa (or [η]=20 ml/g) of 13% and 5% DM. The formulations areas following:

Group 1: HA-VS at 0.81 mg/ml, and Dextran-SH at 13% DM and at from about 0.1 mg/ml to about 0.35 mg/ml, respectively.

Group 2: HA-VS at 0.81 mg/ml, and Dextran-SH at 5% DM and at from about 0.1 mg/ml to about 0.35 mg/ml, respectively.

Group 3: HA-VS at 0.65 mg/ml, and Dextran-SH at 13% DM and at from about 0.1 mg/ml to about 0.35 mg/ml, respectively.

Group 4: HA-VS at 0.65 mg/ml, and Dextran-SH at 5% DM and at from about 0.1 mg/ml to about 0.35 mg/ml, respectively.

The G' and G" value at 5 rad/s frequency and 5% strain were shown. These results showed that the mechanical strength decreased as HA-VS concentration decreased, decreased as Dextran-SH (Dex-SH) degree of modification decreased, and decreased as Dextran-SH concentration decreased, respectively. G' of desirable value could be adjust by adjusting the DM and concentration of the hydrogel forming polymers.

TABLE 12

| Mechanical properties of Gel | | | | |
|---|---|---|---|---|
| | HA-VS:Dex-SH molar ratio | Conc of Dextran-SH (mg/ml) | G' (Pa) | G" (Pa) |
| Group 1 | 1:25.0 | 0.35 | 0.39 | 0.063 |
| | 1:20.0 | 0.28 | 0.35 | 0.083 |
| | 1:15.7 | 0.22 | 0.26 | 0.095 |
| | 1:12.8 | 0.18 | 0.24 | 0.098 |
| | 1:10.0 | 0.14 | 0.11 | 0.081 |
| | 1:7.1 | 0.10 | No gel | |
| Group 2 | 1:25.0 | 0.35 | 0.26 | 0.10 |
| | 1:20.0 | 0.28 | 0.32 | 0.12 |
| | 1:15.7 | 0.22 | 0.15 | 0.099 |
| | 1:12.8 | 0.19 | No gel | |
| Group 3 | 1:31.1 | 0.28 | 0.13 | 0.053 |
| | 1:24.9 | 0.22 | 0.10 | 0.058 |
| | 1:19.6 | 0.18 | 0.042 | 0.044 (no gel) |
| Group 4 | 1:31.1 | 0.35 | 0.11 | 0.061 |
| | 1:24.9 | 0.28 | 0.094 | 0.062 |
| | 1:19.6 | 0.22 | 0.040 | 0.054 (no gel) |
| | 1:16.0 | 0.18 | No gel | |

5.4 Hydrogels Formed by PEG-SH

Another hydrogel was formed by using a large [η] polymer (HA-VS of 2.6 MD, prepared as Example 2.1, [η]=2960 ml/g) was mixed with a small [η] PEG-thiol (PEG-SH).

Another hydrogel was formed by using a large [η] polymer (HA-VS of 2.6 MD, prepared as Example 2.1, [η]=2960 ml/g) was mixed with a small [η] four-arm PEG thiol (5 KDa, [η]~10 ml/g, obtained from commercial purchase). In this example, HA-VS was kept at 0.8 mg/ml and PEG dithiol was 0.4 mg/ml (Sample 1), 0.2 mg/ml (Sample 2) and 0.1 mg/ml (Sample 3). Examples of mechanical properties measured at 5% strain are shown in Table 13:

TABLE 13

| Mechanical properties of Gel | | | | | |
|---|---|---|---|---|---|
| | HA-VS:PEG-SH | 1 rad/s | | 10 rad/s | |
| | molar ratio | G'(Pa) | G"(Pa) | G'(Pa) | G"(Pa) |
| Sample 1 | 1:260 | 0.98 | 0.05 | 0.98 | 0.09 |
| Sample 2 | 1:130 | 0.71 | 0.07 | 0.81 | 0.15 |
| Sample 3 | 1:65 | 0.20 | 0.06 | 0.27 | 0.18 |

Example 6 Measuring the Mechanical Properties of Hydrogel by Modified High [η] Polymer and Modified Low [η] Polymer HA-VS, HA-SH and Dextran-SH was made according to Example 2. Hydrogels were formed and loaded to a rheometer according to Example 5. Four representative formulations as shown in Table 14 of the hydrogel were shown as examples for illustration purpose. The HA-VS to SH polymer molar ratio was 1:62, 1:12, 1:10, 1:16 for F1 to F4 accordingly.

TABLE 14

| Formulations of hydrogel | | | | | | | | |
|---|---|---|---|---|---|---|---|---|
| | | | | | SH polymer | | | |
| | VS polymer | | | | | MW | DM | |
| Code | Type | MW | DM | Concentration | Type | (kDa) | (%) | Concentration |
| F1 | HA | 2.6 MDa | 23% | 0.50 mg/ml | HA | 65 | 14% | 0.78 mg/ml |
| F2 | | | | 0.80 mg/ml | HA | 65 | 14% | 0.24 mg/ml |
| F3 | | | | 0.81 mg/ml | Dextran | 45 | 12.8% | 0.14 mg/ml |
| F4 | | | | 0.65 mg/ml | Dextran | 45 | 12.8% | 0.18 mg/ml |

The mechanical properties of the hydrogels under different type of mechanical tasting modes were measured. Examples of tests were shown in FIG. 14 to FIG. 17.

Figure 14A:
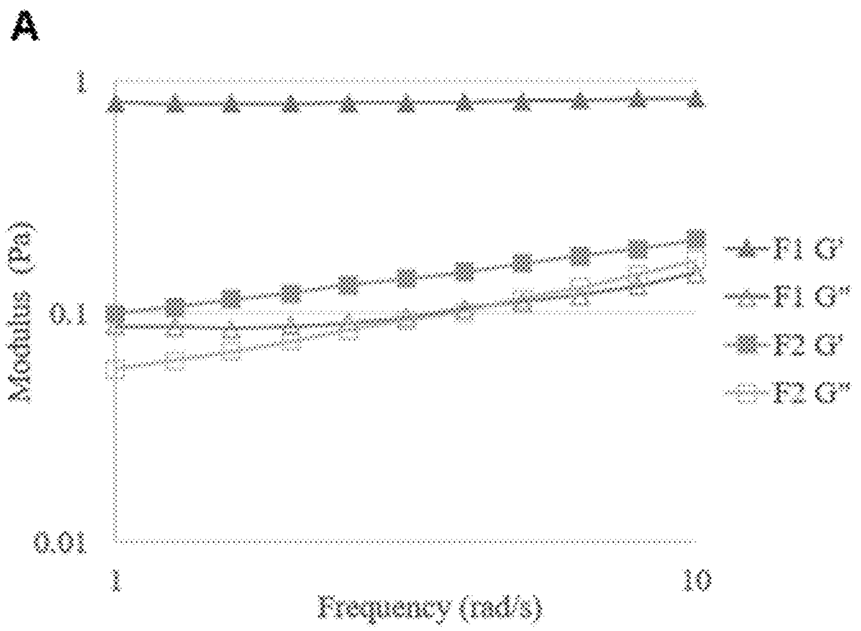
FIGS. 14A and 14B illustrate the G' and G" of four hydrogels undergoing frequency swept test.
Figure 14B:
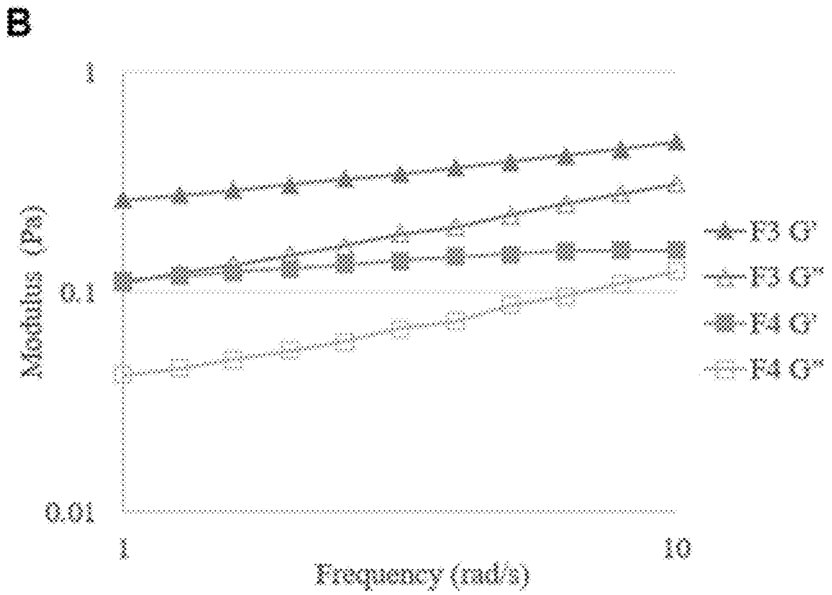

FIG. 14A and FIG. 14B showed the result of frequency sweep tests. In this test, the oscillatory strain was kept at 5% and the mechanical properties, for example G' and G", were measured at different oscillatory frequency. This test demonstrated that despite the very low G' value, hydrogels were viscoelastic solid instead of viscous liquid because the G' is higher than G" even at low frequency.

Figure 15A:
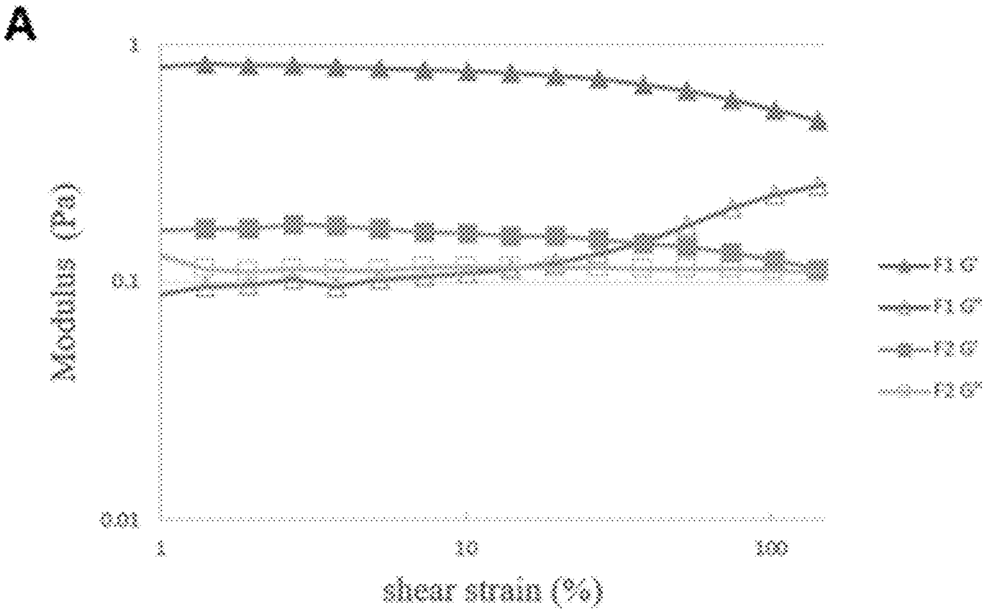
FIGS. 15A and 15B illustrate the G' and G" of four hydrogels undergoing strain swept test.
Figure 15B:
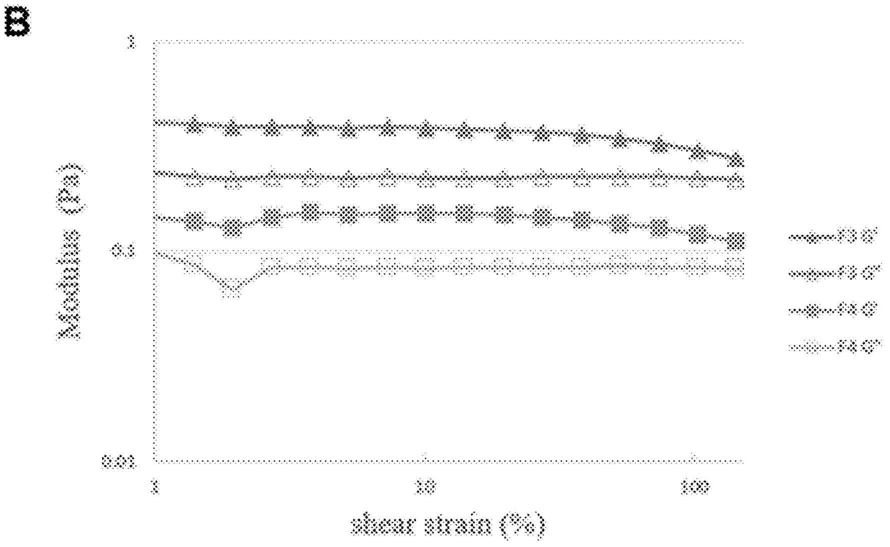

FIG. 15A and FIG. 15B showed the result of strain sweep test. In this test, the oscillatory frequency was kept at 5 rad/s and the mechanical properties, for example G' and G", were measured at different oscillatory strain. This test demonstrated that the linear viscoelastic range (LVR) of the hydrogels. For hydrogel having similar G' at low shear strain (e.g. F2 and F4 at 1%), their behavior at high strain (e.g. 100%) can be different. F2 is significantly less elastic (e.g. G'~G") compares to F4. The result showed that the elastic behavior under different strain is adjustable.

Figure 16A:
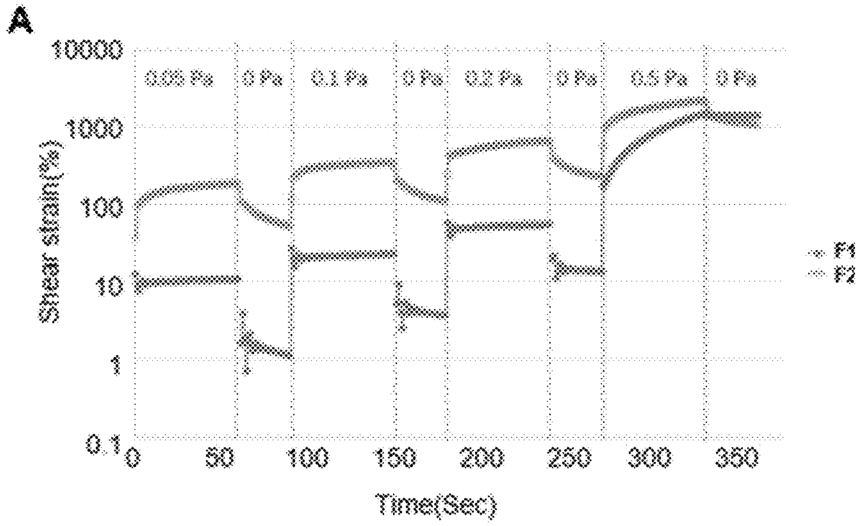
FIGS. 16A and 16B illustrate the strain response of four hydrogels undergoing step stress test.
Figure 16B:
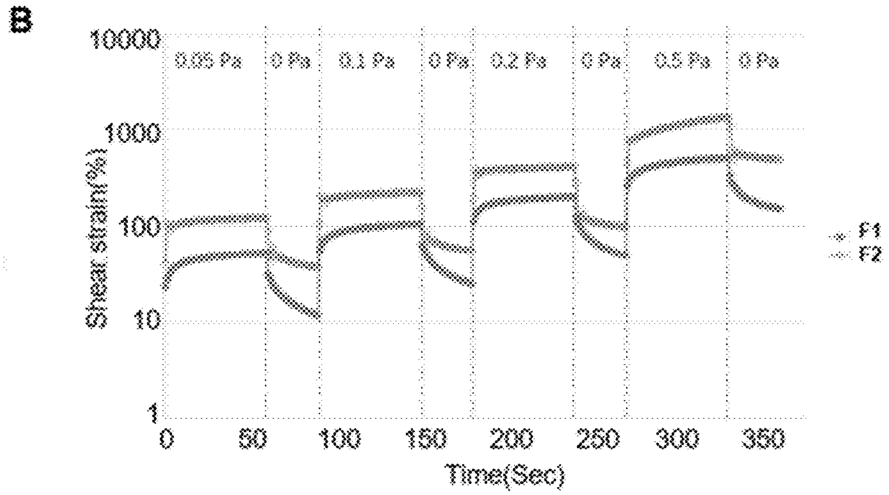

FIG. 16A and FIG. 16B showed the result of step stress tests. In a step stress test, a constant stress was applied on the material and the resulting strain was measured. In this test, we first applied a constant stress for 60 seconds, and followed by 30 seconds of 0 Pa (relaxation). Afterwards, a second constant stress was applied and followed by another relaxation. Four stresses, 0.05 Pa, 0.1 Pa, 02 Pa and 0.5 Pa were applied stepwise to the hydrogel. The result showed that the material is indeed a viscoelastic solid at low stress condition because the material's strain remained almost constant for each stress. If the material is a viscous solution, the strain response will be expected to increase at a constant rate for each stress applied. Another evidence showing the solid properties of the hydrogel at low stress is that as the stress is removed (relaxation), the hydrogel returned to the more or less initial position with elastic ringing, similar to the bouncing movement of a spring once a load was removed instantaneously. In our examples, most of the hydrogels were relatively more elastic (the strain was more constant, the relaxation was more prominent) at low stress level, but relatively more viscous (the strain was increasing, and the relaxation was less prominent) at higher stress level. A hydrogel having high elasticity at low stress does not necessarily corresponds to a high elasticity at high stress. For example, F1 is more elastic compares to the other hydrogels (e.g. the strain was only 10%) at 0.05 Pa, but are more viscous (e.g. the strain rate is higher) at 0.5 Pa.

Figure 17A:
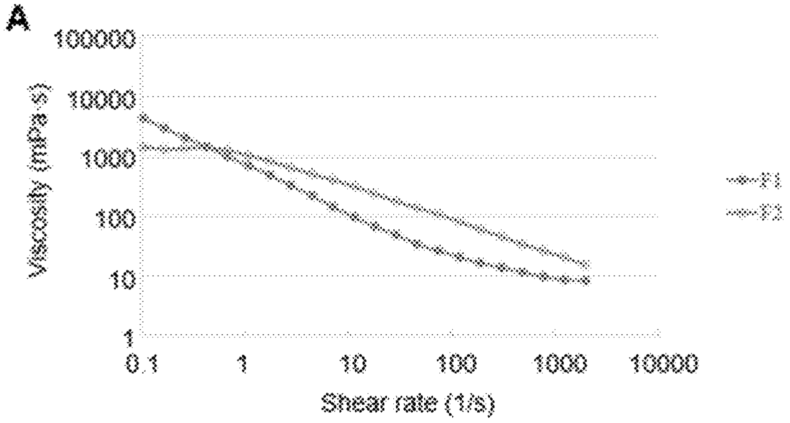
FIGS. 17A and 17B illustrate the shear viscosity of four hydrogels undergoing continuous shear test.
Figure 17B:
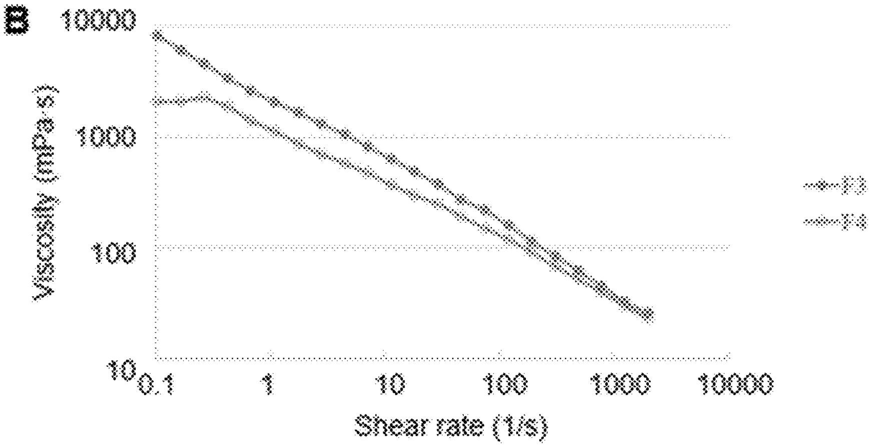

FIG. 17A and FIG. 17B was the result of a continuous shear test. In this test, the shear viscosity of the material was measured at different shear rates. The results showed that the hydrogels' viscosity was decreased as the shear rate increased. For most hydrogels, the shear viscosity at low shear rate (e.g. 0.1/s) was at least 1000 mPa·s and the shear viscosity at high shear rate (e.g. 1000/s) was lower than 100 mPa. The viscosity at 0.1/s was about 4200 mPa·s, 1400 mPa·s, 8100 mPa·s and 2100 mPa·s for F1, F2, F3 and F4 accordingly. The viscosity at 1000/s was about 9 mPa·s, 23 mPa·s, 32 mPa·s and 30 mPa·s for F1, F2, F3 and F4 accordingly. Some hydrogel has higher viscosity at low shear rate but lower viscosity at high shear rate, for example comparing F1 to F2.

Example 7 Synthesis of Maleimide Modified Hyaluronic Acid (HA-MI)

Hyaluronic acid (HA) with molecular weight 2.6 MDa was obtained from Bloomage Freda (Jinan, China).

N-(2-aminoethyl) maleimide trifluoroacetic acid (MI) and 4-(4,6-Dimethoxy-1,3,5-triazin yl)-4-methylmorpholinium chloride (DMTMM) was obtained from Aladdin Biotechnology.

MI molecule (15.10 mg) was added into a solution containing HA (24 mg) in 8 ml of 1 mM PB. About 350 μl of 0.1M NaOH was then added into the mixture to adjust the pH to 6.0 before the addition of DMTMM (66.4 mg). The molar ratio of —COOH from HA to —NH2 from MI to DMTMM was 1:1:4. The reaction was stopped in 72 h by precipitation in 32 mL of ethanol in a 50 mL conical tube after addition of 320 μL of 25% NaCl. The precipitate was separated via centrifugation at 8000 rpm for 5 min and decanting of the supernatant liquid. The residue pellet was re-dissolved in 10 mL of DI and further purified by dialysis in 4 L of DI for three days. The dialysis buffer was changed twice a day. The concentration of HA-MI in DI after dialysis was 1.6 mg/ml, the DM was 4.8%.

Example 8 Formation of Hydrogel from HA-MI

HA-MI made from example 7 was mixed with HA-SH of 65 kDa and 11.6% DM in a phosphate buffer. The final concentration was 1.1 mg/ml HA-MI, 1 mg/ml HA-SH at 0.02M phosphate buffered saline of about 300 mOsm. A hydrogel was formed.

Example 9 Encapsulation of Active Pharmaceutical Ingredient (API) in Hydrogel

HA-VS, HA-SH and Dextran-SH was made according to Example 2. Hydrogels were formed similar to Example 5, except that API in powder form was added to the polymer mixture before hydrogel formation. 19 representative formulations of hydrogel were shown in Table 15 for illustration purpose. The mechanical properties of four representative formulations, as measured according to Example 5, were shown in Table 16.

TABLE 15

Formulations of hydrogel

| | VS Polymer | | | | SH Polymer | | | | API | | |
|---|---|---|---|---|---|---|---|---|---|---|---|
| Hydrogel | Type | MW (MDa) | DM (%) | Conc. (mg/ml) | Type | MW (kDa) | DM (%) | Conc. (mg/ml) | Type | Conc. (%) | Other ingredient |
| A1 | HA | 2.6 | 27% | 0.5 | Dextran | 40 | 12.8 | 0.24 | Moxifloxacin | 0.5 | N/A |
| A2 | | | | | | | | | Fluconazole | 0.5 | |
| A3 | | | | | | | | | Polymyxin B | 0.2 | |
| A4 | | | | | | | | | tobramycin | 0.3 | |
| A5 | | | | | | | | | dexamethasone | 0.1 | |
| A6 | | | | | | | | | Amikacin | 0.25 | |
| A7 | | | | | | | | | cyclosporine | 0.1 | Cremophor |
| A8 | | | | | | | | | Tacrolimus | 0.1 | EL |
| A9 | | | | | HA | 65 | 14 | 0.24 | Moxifloxacin | 0.5 | N/A |
| A10 | | | | | | | | | Fluconazole | 0.5 | |
| A11 | | | | | | | | | dexamethasone | 0.1 | |
| A12 | | | | | | | | | Amikacin | 0.25 | |
| A13 | | | | | | | | | cyclosporine | 0.1 | Cremophor |
| A14 | | | | | | | | | Tacrolimus | 0.1 | EL |
| A15 | | | 20% | 0.8 | Dextran | 40 | 5.6 | 0.3 | Benzylamine | 0.1 | N/A |
| A16 | | | | | | | | | Levofloxacin | 0.5 | |
| A17 | | | | | | | | | Polymyxin B | 0.2 | |
| A18 | | | | | | | | | tobramycin | 0.1 | |

TABLE 16

Mechanical properties of hydrogel

| Hydrogel | G' (Pa) | G" (Pa) |
|---|---|---|
| A15 | 0.17 | 0.06 |
| A16 | 0.17 | 0.05 |
| A17 | 0.21 | 0.06 |
| A18 | 0.12 | 0.05 |

Example 10 Release of API from Hydrogel

Moxifloxacin was obtained from Hetero Drugs Limited. Levofloxacin was obtained from Aladdin Biotechnology. Bevacizumab was obtained from Roche. Modified RNA aptamer was obtained from Synbio Tech Inc.

10.1 Release of Moxifloxacin

The following formulation (Table 17) was for the formation of hydrogel with moxifloxacin.

TABLE 17

Formulations of hydrogel with moxifloxacin

| VS Polymer | | | | SH Polymer | | | | API |
|---|---|---|---|---|---|---|---|---|
| Type | MW (MDa) | DM (%) | Conc. (mg/ml) | Type | MW (kDa) | DM (%) | Conc. (mg/ml) | Conc. (%) |
| HA | 2.6 | 27 | 0.8 | Dextran | 40 | 5.6 | 0.3 | 0.5 |

Figure 18:
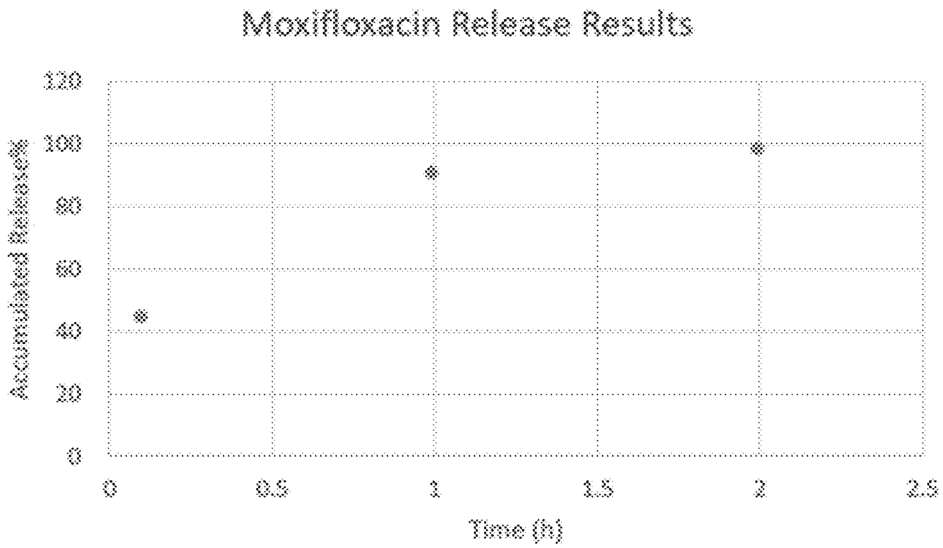
FIG. 18 illustrates the release of a small molecule Moxifloxacin from hydrogel.

Hydrogel was formed according to Example 5. The gel was incubated at 37° C. for 2 days before release experiment. For the release experiment, a small portion of the gel (between 200-300 μg) were transferred by a 3 mL disposable plastic pipettes into a 5 ml Eppendorf tube at ambient temperature. The mass of the gel was measured for the final release calculation. The Eppendorf tube was then slowly filled up with 5 ml of PBS solutions to minimize the disturbing of gel. The release experiment was performed at 37° C. At each predetermined time point, 0.1 h, 1 h, and 2 h in this case, the tube was gently shake for 10 s and sit at ambient temperature for 10 min before 100 μl of releasing buffer were taken for high performance liquid chromatography (HPLC) quantification. Prior to the injection, the releasing buffer was diluted 10 times with 0.1M PB and filtered through a 0.22 μm syringe filter. HPLC was performed with a mobile phase consisting of 0.05 M dipotassium phosphate/acetonitrile (82/18, v/v, pH=3) at a flow rate of 1.0 ml/min at 37° C. The eluent flowed through a YMC-Park Pro C18 column (4.6 mm×150 mm, 3 um) and the detection wavelength was at 293 nm. The concentrations were measured using Moxifloxacin as standard with linear range of 2, 5, 10, 25, 50, 100 μg/ml. The experiments were performed in triplicate. FIG. 18 showed that the moxifloxacin was rapidly released and continued for about 2 hours.

10.2 Release of Levofloxacin

Figure 19:
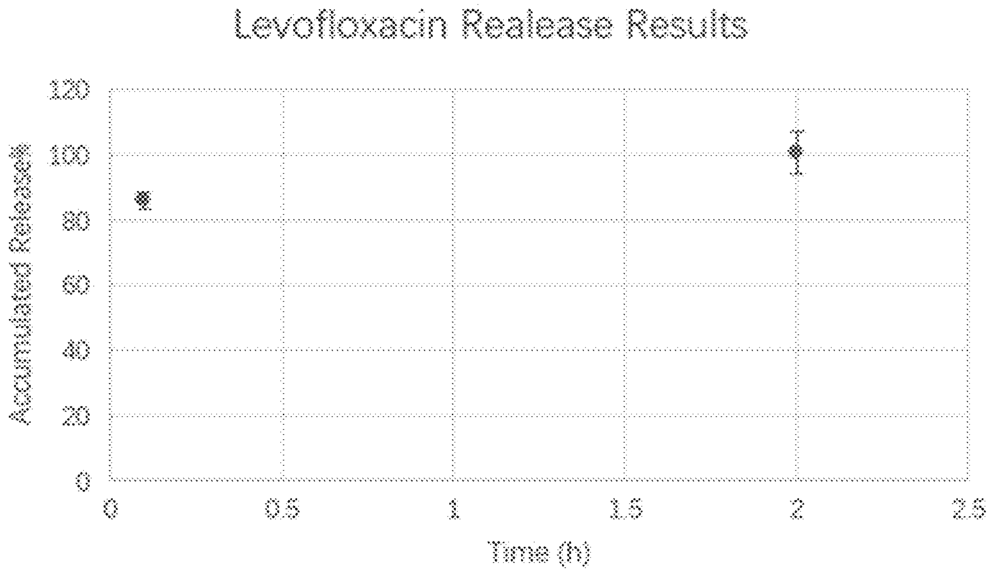
FIG. 19 illustrates the release of a small molecule Levofloxacin from hydrogel.

The following formulation (Table 18) was for the formation of hydrogel with Levofloxacin. The hydrogel with Levofloxacin was formed according to 10.1. The concentrations were measured using Levofloxacin as standard with linear range of 2, 5, 10, 25, 50, 100 μg/ml. FIG. 19 showed that the Levofloxacin was rapidly released and continued for about 2 hours.

TABLE 18

Formulations of hydrogel with Levofloxacin

| VS Polymer | | | | SH Polymer | | | | API |
|---|---|---|---|---|---|---|---|---|
| Type | MW (MDa) | DM (%) | Conc. (mg/ml) | Type | MW (kDa) | DM (%) | Conc. (mg/ml) | Conc. (%) |
| HA | 2.6 | 20 | 0.8 | Dextran | 40 | 5.6 | 0.3 | 0.5 |

10.3 Release of IgG Protein

The following formulation (Table 19) was for the formation of hydrogel with a protein drug bevacizumab.

TABLE 19

Formulations of hydrogel with bevacizumab

| VS Polymer | | | | SH Polymer | | | | API |
|---|---|---|---|---|---|---|---|---|
| Type | MW (MDa) | DM (%) | Conc. (mg/ml) | Type | MW (kDa) | DM (%) | Conc. (mg/ml) | Conc. (%) |
| HA | 2.6 | 18.3 | 0.75 | HA | 65 | 12 | 0.25 | 0.25 |

Figure 20:
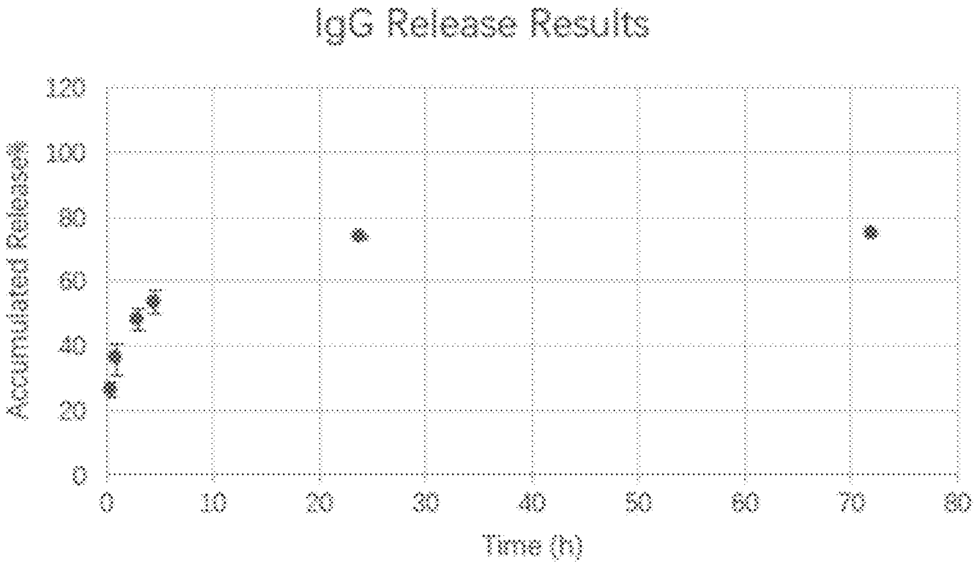
FIG. 20 illustrates the release of a protein Bevacizumab from hydrogel.

Hydrogel was formed similar to Example 5. Bevacizumab was used as a protein drug example. 200 ul of Avastin (purchased from Roche, USA) which contains 25 mg/ml Bevacizumab, was mixed with 926 ul 1.62 mg/ml HA-VS and 40.5 ul 12.4 mg/ml HA-SH, with 200 ul 0.5M phosphate buffer and appropriate amount of double deionized water to the final formulation according to table 18. The gel was incubated at 37° C. for 2 days before release experiment. For the release experiment, a small portion of gel (between 200-330 μg) were transferred by a 3 mL disposable plastic pipettes into a 10 ml glass vial at ambient temperature, and the mass was measured for the final release calculation. The glass vial was slowly filled up with 8 ml of a release buffer (PBS solutions containing 40 mM arginine pH adjusted to 7.4) to minimize the disturbing of gel. The release was performed at 37° C. At each predetermined time point, 0.5 h, 1 h, 3 h, 4.5 h, 24 h, and 72 h in this case, the sample was gently shake for 10 s and sit at ambient temperature for 10 min before 400 μl of releasing buffer were taken for HPLC quantification. Prior to the injection, the releasing buffer was filtered through a 0.22 μm syringe filter. HPLC was performed with a phosphate buffer consisting of 0.2 M potassium phosphate and 0.25 M potassium chloride (pH=6.2) at a flow rate of 0.5 ml/min at 30° C. The eluent with injection volume 50 μl flowed through a Vanguard Cartridges Holder column and a Waters Xbridge Protein BEH SEC column (7.8 mm×300 mm, 200 A, 3.5 μm) in series and the detection wavelength was at 280 nm. The concentrations were measured using Bevacizumab as standard with linear range of 12.5, 25, 50, 100 μg/ml. The experiments were performed in triplicate. FIG. 20 showed that the bevacizumab was rapidly released in about 5 hours and continue to release for about 1-3 days.

10.4 Release of Aptamer

The following formulation (Table 20) was for the formation of hydrogel with an RNA based aptamer.

TABLE 20

Formulations of hydrogel with aptamer

| | VS Polymer | | | | SH Polymer | | | | API |
|---|---|---|---|---|---|---|---|---|---|
| Hydrogel | Type | MW (MDa) | DM (%) | Conc. (mg/ml) | Type | MW (kDa) | DM (%) | Conc. (mg/ml) | Conc. (uM) |
| Ap1 | HA | 2.6 | 18.3 | 0.75 | HA | 65 | 12 | 0.25 | 20 |
| Ap2 | HA | 2.6 | 18.3 | 0.8 | Dextran | 40 | 5 | 0.3 | 16.7 |

Figure 21:
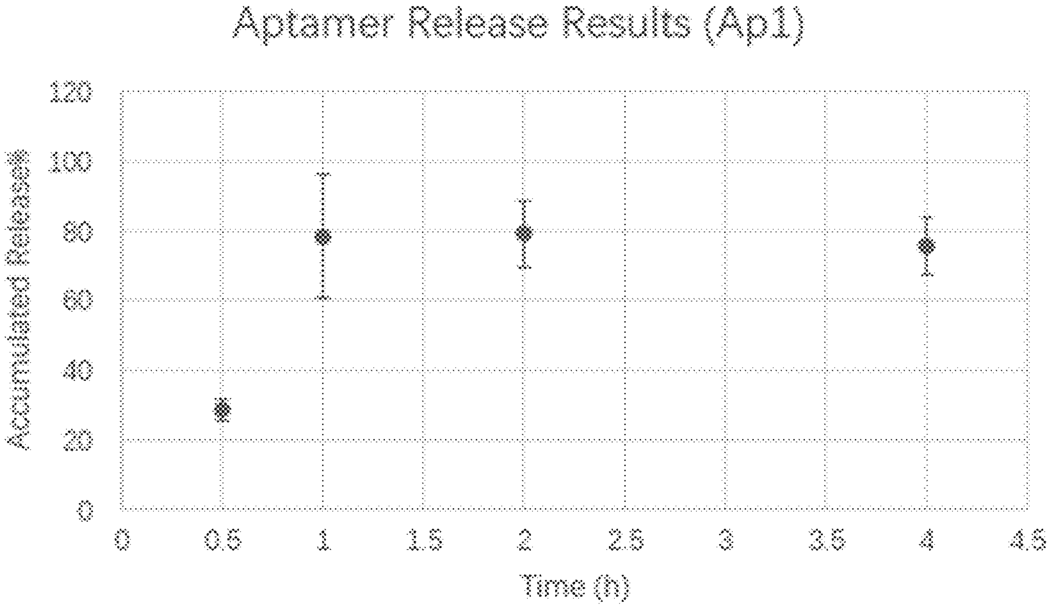
FIG. 21 illustrates the release of an aptamer from hydrogel Ap1.
Figure 22:
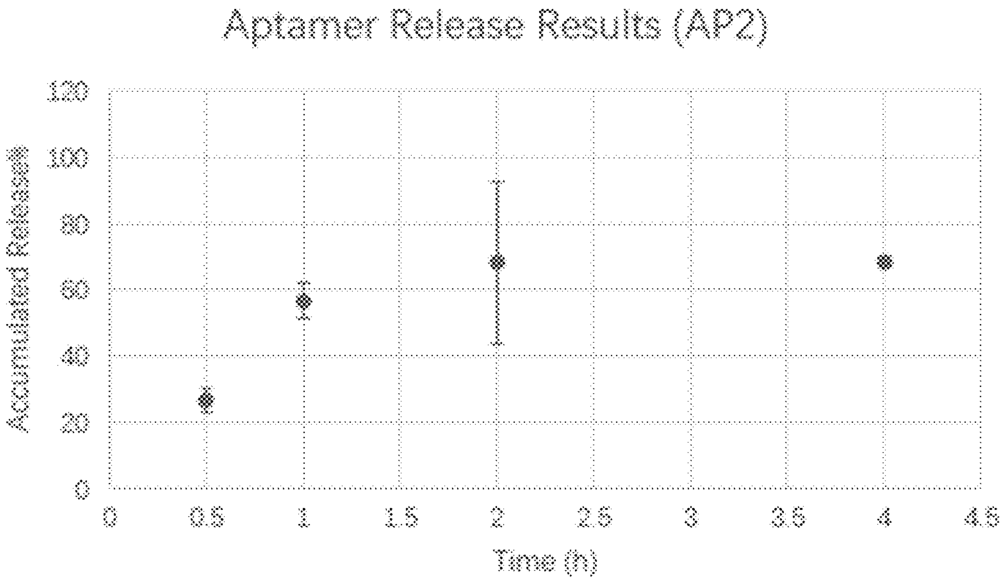
FIG. 22 illustrates the release of an aptamer from hydrogel Ap2.

Hydrogel was formed similar to Example 5. An aptamer similar to Macugen of the following sequence of nucleotides and functional groups: CfGmGmAAUfCfAmGmUfGmA-mAmUfGmCfUfUfAmUfAmCfAmUfCfCfGm3'(SEQ ID NO:1), with 5' end caped with 6 carbon (C6) and 3' end caped with a 3'-dT-S' and Cy3 fluorescent dye, was used as an aptamer example. Gm or Am and Cf or Uf represent 2-methoxy and 2-fluoro variants of their respective purines and pyrimidines, and C, A, U and G code for cytidylic, adenylic, uridylic and guanylic acids. Hydrogels were formed similar to Example 5, except that the solution before gel formation was added to the API in powder form. The gel was incubated at 37° C. for 2 days before release experiment. For the release experiment, a small portion of gel (between 200-300 μg) were transferred by a 3 mL disposable plastic pipettes into a 10 ml glass vial at ambient temperature, and the mass was measured for the final release calculation. The glass vial was slowly filled up with 5 ml of PBS solutions to minimize the disturbing of gel. The release was performed at 37° C. in triplicate. At each predetermined time point, 0.5 h, 1 h, 2 h, and 4 h in this case, the sample was gently shake for 10 s and sit at ambient temperature for 10 min before 1000 μl of releasing buffer were taken for UV quantification at 260 nm. The experiments were performed in triplicate. FIG. 21 and FIG. 22 showed that the aptamer was released from hydrogel rapidly and continue for about 4 hours.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A composition comprising at least a first polymer having a first reactive group and at least a second polymer having a second reactive group, wherein, said first polymer have an intrinsic viscosity [η] of at least 500 ml/g, said second polymer have an intrinsic viscosity [η] lower than the first polymer and less than 1800 ml/g, said first polymer's concentration in said composition is at most about 5 mg/ml, wherein said first polymer and/or said second polymer is independently selected from the group consisting of a polysaccharide, a poly (acrylic acid), a poly (hydroxyethylmethacrylate), an elastin, a collagen, a polyethylene glycol, a derivative thereof, and any combinations thereof, wherein said first reactive group is selected from the group consisting of a vinyl, an acryloyl, a thiol, an alkene, a thiolester, an isocyanate, an isothiocyanate, an alkyl halide, a sulfonyl halide, an epoxide, an imidoester, a fluorophenyl ester, a carbonate, a carbodiimide, a disulfide, an aziridine and any combinations thereof, and wherein said second reactive group is selected from the group consisting of a thiol, an amine, an azide, a hydrazide, a diene, a hydrazine, a hydroxylamine and any combinations thereof.

2. The composition of claim 1, wherein said first polymer is capable of reacting with said second polymer to form a hydrogel.

3. The composition of claim 1, wherein said first polymer and/or said second polymer is hydrophilic and/or water soluble.

4. The composition of claim 1, wherein said first polymer and/or said second polymer is independently selected from the group consisting of a hyaluronic acid, a guar gum, a starch, a chitosan, a chondroitin sulfate, an alginate, a carboxymethylcellulose, a dextran, a derivative thereof, and any combinations thereof.

5. The composition of claim 1, wherein said first polymer comprises a first polymer derivative, said first polymer derivative comprises the first reactive group, and said first polymer derivative is electrophilic; and/or said second polymer comprises a second polymer derivative, said second polymer derivative comprises the second reactive group, and said second polymer derivative is nucleophilic.

6. The composition of claim 5, wherein said first reactive group is selected from a vinylsulfone, a maleimide, an acrylate, a methacrylate, an epoxide and any combinations thereof.

7. The composition of any of claim 1, wherein said first polymer have a molecular weight of about 500,000 to about 5,500,000 dalton; and/or said second polymer has a molecular weight of about 3,000 to about 800,000 dalton.

8. The composition of claim 1, wherein a molecular weight (MW) ratio between said first polymer and said second polymer in said composition is from about 500:1 to about 1.5:1, a radius of gyration (Rg) ratio between said first polymer and said second polymer in said composition is from about 150:1 to about 1:1, a mass ratio between said first polymer and said second polymer in said composition is from about 20:1 to about 1:20, a molar ratio between said first polymer and said second polymer in said composition is from about 4:1 to about 1:500.

9. The composition of claim 1, wherein said first polymer may have an intrinsic viscosity [$\eta$] of from about 500 ml/g to about 5000 ml/g; and/or said second polymer may have an intrinsic viscosity [$\eta$] of from about 5 ml/g to less than 1800 ml/g.

10. The composition of claim 5, wherein said first polymer or said second polymer derivative has an average degree of modification (DM) of about 3% to about 50%.

11. The composition of claim 5, wherein said first polymer derivative has a first DM, said second polymer derivative has a second DM, and a ratio between said first DM and said second DM is from about 20:1 to about 1:20.

12. The composition of claim 5, wherein said first polymer derivative is a dextran derivative modified with one or more vinylsulfone groups, a hyaluronic acid derivative modified with one or more vinylsulfone groups, a hyaluronic acid derivative modified with one or more maleimide groups, or a combination thereof, and said second polymer derivative is a dextran derivative modified with one or more thiol groups, a hyaluronic acid derivative modified with one or more thiol groups, or a combination thereof.

13. The composition of claim 1, wherein said composition does not comprise any crosslinker different from said first polymer and/or second polymer.

14. A hydrogel formed with the composition of claim 1.

15. A method for generating a hydrogel, comprising:

a) providing the composition of claim 1; and b) subjecting said composition to a condition enabling formation of the hydrogel.

* * * * *